United States Patent
Smiley et al.

(10) Patent No.: US 11,759,313 B2
(45) Date of Patent: Sep. 19, 2023

(54) LENS DELIVERY SYSTEM

(71) Applicant: PowerVision, Inc., Belmont, CA (US)

(72) Inventors: Terah Whiting Smiley, Davis, CA (US); John A. Scholl, San Ramon, CA (US); David John Smith, Highland, CA (US); Russell J. Redmond, Goleta, CA (US); Derek L. Moran, Goleta, CA (US); Barry Cheskin, Los Altos, CA (US); John Reggie, Santa Rosa, CA (US); Gregory Vinton Matthews, San Francisco, CA (US); Claudio Argento, Felton, CA (US)

(73) Assignee: Alcon Inc., Fribourg (CH)

( * ) Notice: Subject to any disclaimer, the term of this patent is extended or adjusted under 35 U.S.C. 154(b) by 1118 days.

(21) Appl. No.: 16/456,434

(22) Filed: Jun. 28, 2019

(65) Prior Publication Data

US 2019/0374335 A1 Dec. 12, 2019

Related U.S. Application Data

(63) Continuation of application No. 15/457,934, filed on Mar. 13, 2017, now Pat. No. 10,350,060, which is a continuation of application No. 14/637,171, filed on Mar. 3, 2015, now abandoned, which is a continuation of application No. 13/835,876, filed on Mar. 15, 2013, now Pat. No. 8,968,396, which is a continuation-in-part of application No. 12/178,565, filed on Jul. 23, 2008, now Pat. No. 8,956,408.

(60) Provisional application No. 61/613,929, filed on Mar. 21, 2012, provisional application No. 60/951,439, filed on Jul. 23, 2007.

(51) Int. Cl.
*A61F 2/16* (2006.01)

(52) U.S. Cl.
CPC ............ *A61F 2/1675* (2013.01); *A61F 2/167* (2013.01); *A61F 2/1678* (2013.01)

(58) Field of Classification Search
CPC ...... A61F 2/1662; A61F 2/167; A61F 2/1675; A61F 2/1678
See application file for complete search history.

(56) References Cited

U.S. PATENT DOCUMENTS

| | | | |
|---|---|---|---|
| 4,111,995 | A | 9/1978 | Nelson |
| 4,251,887 | A | 2/1981 | Anis |
| 4,253,199 | A | 3/1981 | Banko |
| 4,254,509 | A | 3/1981 | Tennant |
| 4,304,895 | A | 12/1981 | Loshaek |

(Continued)

FOREIGN PATENT DOCUMENTS

| | | |
|---|---|---|
| CN | 1200659 | 12/1998 |
| CN | 1283974 | 2/2001 |

(Continued)

OTHER PUBLICATIONS

Baughman et al. "Negative poisson's ratios for extreme states fo matter," *Science*, vol. 288, pp. 2018-2022, Jun. 16, 2000.

(Continued)

*Primary Examiner* — Ashley L Fishback
(74) *Attorney, Agent, or Firm* — Levine Bagade Han LLP

(57) ABSTRACT

Delivery devices for delivering an ophthalmic device into an eye. In some embodiments the delivery devices are adapted to deliver an intraocular lens into an eye.

5 Claims, 19 Drawing Sheets

(56) References Cited

U.S. PATENT DOCUMENTS

| | | |
|---|---|---|
| 4,373,218 A | 2/1983 | Schachar |
| 4,409,691 A | 10/1983 | Levy |
| 4,423,809 A | 1/1984 | Mazzocco |
| 4,435,855 A | 3/1984 | Pannu |
| 4,435,856 A | 3/1984 | L'esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,575,373 A | 3/1986 | Johnson |
| 4,585,457 A | 4/1986 | Kalb |
| 4,600,004 A | 7/1986 | Lopez et al. |
| 4,604,295 A | 8/1986 | Humphreys |
| 4,615,701 A | 10/1986 | Woods |
| 4,620,954 A | 11/1986 | Singer et al. |
| 4,681,102 A | 7/1987 | Bartell |
| 4,685,921 A | 8/1987 | Peyman |
| 4,685,922 A | 8/1987 | Peyman |
| 4,693,717 A | 9/1987 | Michelson |
| 4,702,244 A | 10/1987 | Mazzocco |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,747,404 A | 5/1988 | Jampel et al. |
| 4,763,650 A | 8/1988 | Hauser |
| 4,764,423 A | 8/1988 | Yamaguchi et al. |
| 4,765,329 A | 8/1988 | Cumming et al. |
| 4,781,719 A | 11/1988 | Kelman |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,819,631 A | 4/1989 | Poley |
| 4,834,094 A | 5/1989 | Patton et al. |
| 4,836,201 A | 6/1989 | Patton et al. |
| 4,842,601 A | 6/1989 | Smith |
| 4,848,343 A | 7/1989 | Wallsten et al. |
| 4,862,885 A | 9/1989 | Cumming |
| 4,880,000 A | 11/1989 | Holmes et al. |
| 4,888,012 A | 12/1989 | Horn et al. |
| 4,892,543 A | 1/1990 | Turley |
| 4,902,293 A | 2/1990 | Feaster |
| 4,906,247 A | 3/1990 | Fritch |
| 4,911,158 A | 3/1990 | Weatherly |
| 4,911,714 A | 3/1990 | Poley |
| 4,913,536 A | 4/1990 | Barnea |
| 4,917,680 A | 4/1990 | Poley |
| 4,919,130 A | 4/1990 | Stoy et al. |
| 4,919,151 A | 4/1990 | Grubbs et al. |
| 4,932,966 A | 6/1990 | Christie et al. |
| 4,934,363 A | 6/1990 | Smith et al. |
| 4,946,469 A | 8/1990 | Sarfarazi |
| 4,950,289 A | 8/1990 | Krasner |
| 4,955,889 A | 9/1990 | Van Gent |
| 4,963,148 A | 10/1990 | Sulc et al. |
| 4,988,352 A | 1/1991 | Poley |
| 4,994,082 A | 2/1991 | Richards et al. |
| 4,995,879 A | 2/1991 | Dougherty |
| 4,995,880 A | 2/1991 | Galib |
| 5,007,913 A | 4/1991 | Dulebohn et al. |
| 5,015,254 A | 5/1991 | Greite |
| 5,026,393 A | 6/1991 | Mackool |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,098,439 A | 3/1992 | Hill et al. |
| 5,100,410 A | 3/1992 | Dulebohn |
| 5,123,905 A | 6/1992 | Kelman |
| 5,145,884 A | 9/1992 | Yamamoto et al. |
| 5,145,935 A | 9/1992 | Hayashi |
| 5,152,789 A | 10/1992 | Willis |
| 5,171,241 A | 12/1992 | Buboltz et al. |
| 5,171,266 A | 12/1992 | Wiley et al. |
| 5,176,686 A | 1/1993 | Poley |
| 5,190,552 A | 3/1993 | Kelman |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'donnell |
| 5,290,892 A | 3/1994 | Namdaran et al. |
| 5,304,182 A | 4/1994 | Rheinish et al. |
| 5,326,347 A | 7/1994 | Cumming |
| 5,354,333 A | 10/1994 | Kammann et al. |
| 5,391,590 A | 2/1995 | Gerace et al. |
| 5,405,386 A | 4/1995 | Rheinish et al. |
| 5,425,734 A | 6/1995 | Blake |
| 5,426,166 A | 6/1995 | Usifer et al. |
| 5,443,506 A | 8/1995 | Garabet |
| 5,444,106 A | 8/1995 | Zhou et al. |
| 5,444,135 A | 8/1995 | Cheradame et al. |
| 5,452,932 A | 9/1995 | Griffin |
| 5,468,246 A | 11/1995 | Blake |
| 5,474,562 A | 12/1995 | Orchowski et al. |
| 5,476,514 A | 12/1995 | Cumming |
| 5,489,302 A | 2/1996 | Skottun |
| 5,494,484 A | 2/1996 | Feingold |
| 5,496,328 A | 3/1996 | Nakajima et al. |
| 5,496,366 A | 3/1996 | Cumming |
| 5,499,987 A | 3/1996 | Feingold |
| 5,506,300 A | 4/1996 | Ward et al. |
| 5,512,609 A | 4/1996 | Yang |
| 5,549,614 A | 8/1996 | Tunis |
| 5,556,400 A | 9/1996 | Tunis |
| 5,562,676 A | 10/1996 | Brady et al. |
| 5,567,365 A | 10/1996 | Weinschenk et al. |
| 5,578,081 A | 11/1996 | Mcdonald |
| 5,582,613 A | 12/1996 | Brady et al. |
| 5,584,304 A | 12/1996 | Brady |
| 5,585,049 A | 12/1996 | Grisoni et al. |
| 5,593,436 A | 1/1997 | Langerman |
| 5,607,433 A | 3/1997 | Polla et al. |
| 5,607,472 A | 3/1997 | Thompson |
| 5,616,148 A | 4/1997 | Eagles et al. |
| 5,620,450 A | 4/1997 | Eagles et al. |
| 5,628,795 A | 5/1997 | Langerman |
| 5,633,504 A | 5/1997 | Collins et al. |
| 5,643,276 A | 7/1997 | Zaleski |
| 5,653,715 A | 8/1997 | Reich et al. |
| 5,665,822 A | 9/1997 | Bitler et al. |
| 5,674,282 A | 10/1997 | Cumming |
| 5,676,669 A | 10/1997 | Colvard |
| 5,693,095 A | 12/1997 | Freeman et al. |
| 5,697,973 A | 12/1997 | Peyman et al. |
| 5,702,400 A | 12/1997 | Brown et al. |
| 5,702,402 A | 12/1997 | Brady |
| 5,702,441 A | 12/1997 | Zhou |
| 5,716,364 A | 2/1998 | Makker et al. |
| 5,728,102 A | 3/1998 | Feingold et al. |
| 5,735,858 A | 4/1998 | Makker et al. |
| 5,766,182 A | 6/1998 | Mcdonald |
| 5,772,666 A | 6/1998 | Feingold et al. |
| 5,774,273 A | 6/1998 | Bornhorst |
| 5,776,138 A | 7/1998 | Vidal et al. |
| 5,776,191 A | 7/1998 | Mazzocco |
| 5,776,192 A | 7/1998 | Mcdonald |
| 5,800,442 A | 9/1998 | Wolf et al. |
| 5,800,533 A | 9/1998 | Eggleston et al. |
| 5,803,925 A | 9/1998 | Yang et al. |
| 5,810,834 A | 9/1998 | Heyman |
| 5,843,188 A | 12/1998 | Mcdonald |
| 5,860,984 A | 1/1999 | Chambers et al. |
| 5,868,751 A | 2/1999 | Feingold |
| 5,873,879 A | 2/1999 | Figueroa et al. |

(56) References Cited

U.S. PATENT DOCUMENTS

| | | |
|---|---|---|
| 5,876,440 A | 3/1999 | Feingold |
| 5,891,931 A | 4/1999 | Leboeuf et al. |
| 5,919,197 A | 7/1999 | Mcdonald |
| 5,921,989 A | 7/1999 | Deacon et al. |
| 5,928,282 A | 7/1999 | Nigam |
| 5,941,886 A | 8/1999 | Feingold |
| 5,944,725 A | 8/1999 | Cicenas et al. |
| 5,947,974 A | 9/1999 | Brady et al. |
| 5,947,975 A | 9/1999 | Kikuchi et al. |
| 5,947,976 A | 9/1999 | Van Noy et al. |
| 5,964,802 A | 10/1999 | Anello et al. |
| 5,968,095 A | 10/1999 | Norrby |
| 5,976,150 A | 11/1999 | Copeland |
| 5,984,962 A | 11/1999 | Anello et al. |
| 6,001,107 A | 12/1999 | Feingold |
| 6,010,510 A | 1/2000 | Brown et al. |
| 6,013,101 A | 1/2000 | Israel |
| 6,015,842 A | 1/2000 | Leboeuf et al. |
| 6,022,358 A | 2/2000 | Wolf et al. |
| 6,048,348 A | 4/2000 | Chambers et al. |
| 6,059,791 A | 5/2000 | Chambers |
| 6,074,397 A | 6/2000 | Chambers et al. |
| 6,102,539 A | 8/2000 | Tucker |
| 6,117,171 A | 9/2000 | Skottun |
| 6,124,980 A | 9/2000 | Cerbell |
| 6,129,733 A | 10/2000 | Brady et al. |
| 6,139,576 A | 10/2000 | Doyle et al. |
| 6,143,000 A | 11/2000 | Feingold |
| 6,143,001 A | 11/2000 | Brown et al. |
| 6,160,084 A | 12/2000 | Langer et al. |
| 6,176,878 B1 | 1/2001 | Gwon et al. |
| 6,179,843 B1 | 1/2001 | Weiler |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,241,737 B1 | 6/2001 | Feingold |
| 6,248,111 B1 | 6/2001 | Glick et al. |
| 6,251,114 B1 | 6/2001 | Farmer et al. |
| 6,280,449 B1 | 8/2001 | Blake |
| 6,283,975 B1 | 9/2001 | Glick et al. |
| 6,283,976 B1 | 9/2001 | Portney |
| 6,299,641 B1 | 10/2001 | Woods |
| 6,302,911 B1 | 10/2001 | Hanna |
| 6,312,433 B1 | 11/2001 | Butts et al. |
| 6,322,589 B1 | 11/2001 | Cumming |
| 6,334,862 B1 | 1/2002 | Vidal et al. |
| 6,336,932 B1 | 1/2002 | Figueroa et al. |
| 6,342,073 B1 | 1/2002 | Cumming et al. |
| 6,348,437 B1 | 2/2002 | Avery et al. |
| 6,371,960 B2 | 4/2002 | Heyman et al. |
| 6,387,101 B1 | 5/2002 | Butts et al. |
| 6,387,126 B1 | 5/2002 | Cumming |
| 6,388,043 B1 | 5/2002 | Langer et al. |
| 6,398,789 B1 | 6/2002 | Capetan |
| 6,406,481 B2 | 6/2002 | Feingold et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,447,520 B1 | 9/2002 | Ott et al. |
| 6,450,642 B1 | 9/2002 | Jethmalani et al. |
| 6,464,725 B2 | 10/2002 | Skotton |
| 6,468,282 B2 | 10/2002 | Kikuchi et al. |
| 6,471,708 B2 | 10/2002 | Green |
| 6,488,708 B2 | 12/2002 | Sarfarazi |
| 6,491,697 B1 | 12/2002 | Clark et al. |
| 6,493,151 B2 | 12/2002 | Schachar |
| 6,497,708 B1 | 12/2002 | Cumming |
| 6,503,275 B1 | 1/2003 | Cumming |
| 6,503,276 B2 | 1/2003 | Lang et al. |
| 6,506,195 B2 | 1/2003 | Chambers et al. |
| 6,517,577 B1 | 2/2003 | Callahan et al. |
| 6,528,602 B1 | 3/2003 | Freeman et al. |
| 6,537,283 B2 | 3/2003 | Van Noy |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk et al. |
| 6,601,956 B1 | 8/2003 | Jean et al. |
| 6,605,093 B1 | 8/2003 | Blake |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,723,104 B2 | 4/2004 | Ott |
| 6,730,123 B1 | 5/2004 | Klopotek |
| 6,733,507 B2 | 5/2004 | Mcnicholas et al. |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,921,405 B2 | 7/2005 | Feingold et al. |
| 6,923,815 B2 | 8/2005 | Brady et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,014,641 B2 | 3/2006 | Kobayashi et al. |
| 7,060,094 B2 | 6/2006 | Shahinpoor et al. |
| 7,068,439 B2 | 6/2006 | Esch et al. |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | Mcdonald |
| 7,156,854 B2 | 1/2007 | Brown et al. |
| 7,217,288 B2 | 5/2007 | Esch et al. |
| 7,241,312 B2 | 7/2007 | Lai et al. |
| 7,247,168 B2 | 7/2007 | Esch et al. |
| 7,247,689 B2 | 7/2007 | Makker et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,335,209 B2 | 2/2008 | Meyer |
| 7,416,300 B2 | 8/2008 | Wei et al. |
| 7,429,263 B2 | 9/2008 | Vaquero et al. |
| 7,438,723 B2 | 10/2008 | Esch |
| 7,453,646 B2 | 11/2008 | Lo |
| 7,485,144 B2 | 2/2009 | Esch |
| 7,494,505 B2 | 2/2009 | Kappelhof et al. |
| 7,637,947 B2 | 12/2009 | Smith et al. |
| 7,675,686 B2 | 3/2010 | Lo et al. |
| 7,753,953 B1 | 7/2010 | Yee |

(56) References Cited

U.S. PATENT DOCUMENTS

| | | |
|---|---|---|
| 7,759,408 B2 | 7/2010 | Schorzman et al. |
| 7,763,069 B2 | 7/2010 | Brady et al. |
| 7,776,088 B2 | 8/2010 | Shadduck |
| 7,878,655 B2 | 2/2011 | Salvati et al. |
| 7,971,997 B2 | 7/2011 | Hiramatsu et al. |
| 7,988,290 B2 | 8/2011 | Campbell et al. |
| 7,988,292 B2 | 8/2011 | Neal et al. |
| 7,988,293 B2 | 8/2011 | Raymond et al. |
| 8,048,155 B2 | 11/2011 | Shadduck |
| 8,158,712 B2 | 4/2012 | Your |
| 8,162,927 B2 | 4/2012 | Peyman |
| 8,241,355 B2 | 8/2012 | Brady et al. |
| 8,246,631 B2 | 8/2012 | Pynson |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,382,769 B2 | 2/2013 | Inoue |
| 8,403,941 B2 | 3/2013 | Peterson et al. |
| 8,425,599 B2 | 4/2013 | Shadduck |
| 8,447,086 B2 | 5/2013 | Hildebrand et al. |
| 8,454,688 B2 | 6/2013 | Esch et al. |
| 8,475,526 B2 | 7/2013 | Pynson |
| 8,574,239 B2 * | 11/2013 | Ichinohe ............... A61F 2/1678 606/107 |
| 8,613,766 B2 | 12/2013 | Richardson et al. |
| 8,632,589 B2 | 1/2014 | Helmy |
| 8,668,734 B2 | 3/2014 | Hildebrand et al. |
| 8,758,361 B2 | 6/2014 | Kobayashi et al. |
| 8,888,845 B2 | 11/2014 | Vaquero et al. |
| 8,900,298 B2 | 12/2014 | Anvar et al. |
| 8,956,408 B2 | 2/2015 | Smiley et al. |
| 8,961,601 B2 | 2/2015 | Biddle et al. |
| 8,968,396 B2 | 3/2015 | Matthews et al. |
| 8,992,609 B2 | 3/2015 | Shadduck |
| 9,005,282 B2 | 4/2015 | Chang et al. |
| 9,034,035 B2 | 5/2015 | Betser et al. |
| 9,044,317 B2 | 6/2015 | Hildebrand et al. |
| 9,226,819 B2 | 1/2016 | Downer |
| 9,277,987 B2 | 3/2016 | Smiley et al. |
| 9,456,895 B2 | 10/2016 | Shadduck |
| 9,855,139 B2 | 1/2018 | Matthews et al. |
| 10,350,060 B2 | 7/2019 | Smiley et al. |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133167 A1 | 9/2002 | Harish et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | Mcnicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0186868 A1 | 9/2004 | Kim |
| 2004/0193263 A1 | 9/2004 | Bryan |
| 2004/0230203 A1 | 11/2004 | Yaguchi |
| 2004/0267359 A1 | 12/2004 | Makker et al. |
| 2005/0021139 A1 | 1/2005 | Shadduck |
| 2005/0033308 A1 | 2/2005 | Callahan et al. |
| 2005/0038446 A1 | 2/2005 | Vanderbilt et al. |
| 2005/0049606 A1 | 3/2005 | Vaquero et al. |
| 2005/0080484 A1 | 4/2005 | Marmo et al. |
| 2005/0090612 A1 | 4/2005 | Soane et al. |
| 2005/0113911 A1 | 5/2005 | Peyman |
| 2005/0125000 A1 | 6/2005 | Tourrette et al. |
| 2005/0125055 A1 | 6/2005 | Deacon et al. |
| 2005/0125056 A1 | 6/2005 | Deacon et al. |
| 2005/0131535 A1 | 6/2005 | Woods |
| 2005/0143750 A1 | 6/2005 | Vaquero |
| 2005/0143751 A1 | 6/2005 | Makker et al. |
| 2005/0147735 A1 | 7/2005 | Lowery et al. |
| 2005/0149057 A1 | 7/2005 | Rathert |
| 2005/0165410 A1 | 7/2005 | Zadno-Azizi et al. |
| 2005/0222577 A1 | 10/2005 | Vaquero |
| 2005/0222578 A1 | 10/2005 | Vaquero |
| 2005/0222579 A1 | 10/2005 | Vaquero et al. |
| 2005/0251253 A1 | 11/2005 | Gross |
| 2005/0251254 A1 | 11/2005 | Brady et al. |
| 2005/0259221 A1 | 11/2005 | Marmo |
| 2005/0264756 A1 | 12/2005 | Esch |
| 2005/0283162 A1 | 12/2005 | Stratas |
| 2005/0283164 A1 | 12/2005 | Wu et al. |
| 2006/0020267 A1 | 1/2006 | Marmo |
| 2006/0020268 A1 | 1/2006 | Brady et al. |
| 2006/0036262 A1 | 2/2006 | Hohl |
| 2006/0069433 A1 | 3/2006 | Nun |
| 2006/0085013 A1 | 4/2006 | Dusek et al. |
| 2006/0097413 A1 | 5/2006 | Ghazizadeh et al. |
| 2006/0100703 A1 | 5/2006 | Evans et al. |
| 2006/0116763 A1 | 6/2006 | Simpson |
| 2006/0129129 A1 | 6/2006 | Smith |
| 2006/0134173 A1 | 6/2006 | Liu et al. |
| 2006/0135642 A1 | 6/2006 | Makker et al. |
| 2006/0142780 A1 | 6/2006 | Pynson et al. |
| 2006/0142781 A1 | 6/2006 | Pynson et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |

(56) References Cited

U.S. PATENT DOCUMENTS

| | | |
|---|---|---|
| 2007/0005136 A1 | 1/2007 | Richardson |
| 2007/0021831 A1 | 1/2007 | Clarke |
| 2007/0027538 A1 | 2/2007 | Aharoni et al. |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0118216 A1 | 5/2007 | Pynson |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0208422 A1 | 9/2007 | Walter et al. |
| 2007/0213817 A1 | 9/2007 | Esch et al. |
| 2007/0244561 A1 | 10/2007 | Ben nun |
| 2007/0260157 A1 | 11/2007 | Norrby |
| 2007/0265636 A1 | 11/2007 | Huynh |
| 2008/0004699 A1 | 1/2008 | Ben nun |
| 2008/0015689 A1 | 1/2008 | Esch et al. |
| 2008/0027460 A1 | 1/2008 | Kobayashi |
| 2008/0027537 A1 | 1/2008 | Gerlach et al. |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0058830 A1 | 3/2008 | Cole et al. |
| 2008/0065096 A1 | 3/2008 | Kappelhof et al. |
| 2008/0071286 A1 | 3/2008 | Kobayashi et al. |
| 2008/0097460 A1 | 4/2008 | Boukhny et al. |
| 2008/0119865 A1 | 5/2008 | Meunier et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0200921 A1 | 8/2008 | Downer |
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2009/0005865 A1 | 1/2009 | Smiley et al. |
| 2009/0018512 A1 | 1/2009 | Charles |
| 2009/0018548 A1 | 1/2009 | Charles |
| 2009/0024136 A1 | 1/2009 | Martin et al. |
| 2009/0030415 A1 | 1/2009 | Gogolewski |
| 2009/0030425 A1 | 1/2009 | Smiley et al. |
| 2009/0036898 A1 | 2/2009 | Ichinohe et al. |
| 2009/0076602 A1 | 3/2009 | Ho et al. |
| 2009/0112313 A1 | 4/2009 | Mentak |
| 2009/0118739 A1 | 5/2009 | Kappelhof et al. |
| 2009/0124773 A1 | 5/2009 | Zhou et al. |
| 2009/0149952 A1 | 6/2009 | Shadduck |
| 2009/0171366 A1 | 7/2009 | Tanaka |
| 2009/0204123 A1 | 8/2009 | Downer |
| 2009/0228101 A1 | 9/2009 | Zadno-Azizi |
| 2009/0234366 A1 | 9/2009 | Tsai et al. |
| 2009/0234449 A1 | 9/2009 | De juan et al. |
| 2009/0248154 A1 | 10/2009 | Dell |
| 2009/0264998 A1 | 10/2009 | Mentak et al. |
| 2009/0270876 A1 | 10/2009 | Hoffmann et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0318933 A1 | 12/2009 | Anderson |
| 2009/0319040 A1 | 12/2009 | Khoury |
| 2010/0016963 A1 | 1/2010 | Park |
| 2010/0039709 A1 | 2/2010 | Lo |
| 2010/0063588 A1 | 3/2010 | Park |
| 2010/0094412 A1 | 4/2010 | Wensrich |
| 2010/0131058 A1 | 5/2010 | Shadduck |
| 2010/0161049 A1 | 6/2010 | Inoue |
| 2010/0179653 A1 | 7/2010 | Argento et al. |
| 2010/0204705 A1 | 8/2010 | Brown et al. |
| 2010/0228344 A1 | 9/2010 | Shadduck |
| 2010/0228346 A1 | 9/2010 | Esch |
| 2010/0324671 A1 | 12/2010 | Shadduck |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2012/0022547 A1 | 1/2012 | Hildebrand et al. |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0221102 A1 | 8/2012 | Tanaka et al. |
| 2012/0226351 A1 | 9/2012 | Peyman |
| 2012/0245591 A1 | 9/2012 | Matthews |
| 2012/0253458 A1 | 10/2012 | Geraghty et al. |
| 2012/0253459 A1 | 10/2012 | Reich et al. |
| 2013/0053954 A1 | 2/2013 | Rao et al. |
| 2013/0060331 A1 | 3/2013 | Shadduck |
| 2013/0103146 A1 | 4/2013 | Smiley et al. |
| 2013/0128368 A1 | 5/2013 | Costache et al. |
| 2013/0131794 A1 | 5/2013 | Smiley et al. |
| 2013/0184816 A1 | 7/2013 | Hayes |
| 2013/0250239 A1 | 9/2013 | Hildebrand et al. |
| 2013/0268070 A1 | 10/2013 | Esch et al. |
| 2013/0317607 A1 | 11/2013 | Deboer et al. |
| 2014/0012277 A1 | 1/2014 | Matthews et al. |
| 2014/0121768 A1 | 5/2014 | Simpson |
| 2014/0142587 A1 | 5/2014 | Walter et al. |
| 2014/0142588 A1 | 5/2014 | Hildebrand et al. |
| 2014/0228949 A1 | 8/2014 | Argento et al. |
| 2014/0249625 A1 | 9/2014 | Shadduck |
| 2014/0257478 A1 | 9/2014 | Mccafferty |
| 2014/0330375 A1 | 11/2014 | Mccafferty |
| 2015/0087743 A1 | 3/2015 | Anvar et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0038278 A1 | 2/2016 | Matthews |
| 2016/0113761 A1 | 4/2016 | Nishi et al. |
| 2016/0128826 A1 | 5/2016 | Silvestrini et al. |
| 2016/0128827 A1 | 5/2016 | Zhao |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2017/0020662 A1 | 1/2017 | Shadduck |
| 2017/0079773 A1 | 3/2017 | Matthews et al. |
| 2018/0028308 A1 | 2/2018 | Smiley et al. |

FOREIGN PATENT DOCUMENTS

| | | |
|---|---|---|
| CN | 1367667 | 9/2002 |
| CN | 1378440 | 11/2002 |
| CN | 1384727 | 12/2002 |
| CN | 101039635 | 9/2007 |
| CN | 101277659 | 10/2008 |
| CN | 102271622 | 12/2011 |
| CN | 202288610 | 7/2012 |
| EP | 0898972 | 3/1999 |
| EP | 1332731 | 8/2003 |
| EP | 1356791 | 10/2003 |
| EP | 1659991 | 5/2006 |
| EP | 2060243 | 5/2009 |
| EP | 2074962 | 7/2009 |
| EP | 2192934 | 6/2010 |
| EP | 2346441 | 7/2011 |
| FR | 2655841 | 6/1991 |
| FR | 2784575 | 12/2000 |
| JP | 07-044938 | 5/1995 |
| JP | 08-501715 | 2/1996 |
| JP | 85-01715 | 2/1996 |
| JP | 08-224295 | 9/1996 |
| JP | 82-24295 | 9/1996 |
| JP | 09-294754 | 11/1997 |
| JP | 92-94754 | 11/1997 |
| JP | 10-206609 | 8/1998 |
| JP | 11-047168 | 2/1999 |
| JP | 1999-047168 | 2/1999 |
| JP | 11-056998 | 3/1999 |
| JP | 11-169391 | 6/1999 |
| JP | 11-276509 | 10/1999 |
| JP | 11-332903 | 12/1999 |

(56) References Cited

FOREIGN PATENT DOCUMENTS

| | | |
|---|---|---|
| JP | 11-47168 | 9/2000 |
| JP | 2001-502592 | 2/2001 |
| JP | 2003-144387 | 5/2003 |
| JP | 2003-524503 | 8/2003 |
| JP | 2003-530978 | 10/2003 |
| JP | 2006-341094 | 12/2006 |
| JP | 2007-513715 | 5/2007 |
| JP | 2007-518447 | 7/2007 |
| JP | 2008-531069 | 8/2008 |
| JP | 2008-534111 | 8/2008 |
| JP | 2009-034451 | 2/2009 |
| JP | 2008-307394 | 6/2010 |
| SU | 1810052 | 4/1993 |
| WO | WO 1995/002378 | 1/1995 |
| WO | WO 1997/006751 | 2/1997 |
| WO | WO-9921513 A1 * 5/1999 ........... A61F 2/1664 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2005/018504 | 3/2005 |
| WO | WO 2005/084588 | 9/2005 |
| WO | WO 2006/004707 | 1/2006 |
| WO | WO 2006/047383 | 5/2006 |
| WO | WO 2006/088440 | 8/2006 |
| WO | WO 2007/005529 | 1/2007 |
| WO | WO 2007/005692 | 1/2007 |
| WO | WO 2007/030095 | 3/2007 |
| WO | WO 2007/061688 | 5/2007 |
| WO | WO 2007/128423 | 11/2007 |
| WO | WO 2007/138564 | 12/2007 |
| WO | WO 2009/015240 | 1/2009 |
| WO | WO 2009/100322 | 8/2009 |
| WO | WO 2009/154455 | 12/2009 |
| WO | WO 2011/119334 | 9/2011 |
| WO | WO 2012/006186 | 1/2012 |
| WO | WO 2012/015300 | 2/2012 |
| WO | WO 2012/129419 | 9/2012 |
| WO | WO 2014/095611 | 6/2014 |

OTHER PUBLICATIONS

Baughman, "Avoiding the shrink," *Nature*, vol. 425, pp. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

Dubbelman et al. "The Thickness of the Aging Human Lens Obtained from Corrected Scheimpflug Images," *Optometry & Vision Science*; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

Hildebrand et al.; U.S. Appl. No. 15/760,640 entitled "Intraocular lenses and methods of manufacturing," filed Mar. 16, 2018.

Hildebrand et al.; U.S. Appl. No. 15/635,080 entitled "Intraocular lens delivery devices and methods of use," filed Jun. 27, 2017.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," Science; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, pp. 551, Oct. 23, 1987.

Lakes, "No contractile obligations," *Nature*, vol. 358, pp. 713-714, Dec. 31, 1992.

Langenbucher et al., "Computerized calculation scheme for toric intraocular lenses," *Acta Ophthalmologica Scandinavica*, vol. 82, No. 3, pp. 270-276, Jun. 2004.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

Qiao et al.; Bio-inspired accommodating fluidic intraocular lens; *Optics Letters*; vol. 34; No. 20; pp. 3214-3216; Oct. 15, 2009.

Rosales et al.; Pentacam Scheimpflug Quantitativelmaging of the Crystalline Lens andIntraocular Lens; J. Refractive Surgery; vol. 25; pp. 421-428; May 2009.

Shadduck, John; U.S. Appl. No. 14/675,245 entitled "Intraocular lens system and method for power adjustment," filed Mar. 31, 2015.

Shadduck, John; U.S. Appl. No. 14/278,249 entitled "Accommodating intraocular lens," filed May 15, 2014.

Smiley et al.; U.S. Appl. No. 15/345,020 entitled "Accommodating intraocular lenses," filed Nov. 7, 2016.

Smiley et al.; U.S. Appl. No. 15/457,934 entitled "Lens delivery system," filed Mar. 13, 2017.

Smith et al.; U.S. Appl. No. 15/000,783 entitled "Accommodating intraocular lens system having spherical aberration compensation and method," filed Jan. 19, 2016.

Takahashi et al., "Structure and properties of shape-memory polyurethane block copolymers," *Journal of Applied Polymer Science*, vol. 60, pp. 1061-1069, May 1996.

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 2003.

Tobushi et al., "Thermomechanical properties of shape memory polymers of polyurethane series and their applications," *Journal de Physique IV, Colloque C1*, vol. 6, pp. 377-384, Aug. 1996.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Engineerring A*, vol. 370, pp. 41-49, Apr. 15, 2004.

(56) References Cited

OTHER PUBLICATIONS

Wang et al., "Extreme stiffness systems due to negative stiffness elements," *American Journal of Physics*, vol. 72, No. 1, pp. 40-50, Jan. 2004.

Wang et al., "Stable extremely-high-damping discrete viscoelastic systems due to native stiffness elements," *Applied Physics Letters*, vol. 84, No. 22, pp. 4451-4453, May 31, 2004.

Wyant et al; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

U.S. Appl. No. 13/835,876, filed Mar. 15, 2013.
U.S. Appl. No. 14/637,171, filed Mar. 3, 2015.
U.S. Appl. No. 15/369,616, filed Dec. 5, 2016.
U.S. Appl. No. 15/457,934, filed Mar. 13, 2017.

\* cited by examiner

LENS DELIVERY SYSTEM

CROSS REFERENCE TO RELATED APPLICATIONS

This application is a continuation of U.S. patent application Ser. No. 15/457,934, filed Mar. 13, 2017, which is a continuation of U.S. application Ser. No. 14/637,171, filed Mar. 3, 2015, now abandoned, which is a continuation of U.S. application Ser. No. 13/835,876, filed Mar. 15, 2013, now U.S. Pat. No. 8,968,396, which claims priority to U.S. Provisional Application No. 61/613,929, filed Mar. 21, 2012; U.S. application Ser. No. 13/835,876 is also a continuation-in-part of U.S. application Ser. No. 12/178,565, filed Jul. 23, 2008, now U.S. Pat. No. 8,956,408, which claims priority to U.S. Provisional Application No. 60/951,439, filed Jul. 23, 2007, the disclosures of each of which are incorporated by reference herein.

This application is related to and incorporates by reference herein the disclosures of the following U.S. patent applications: U.S. application Ser. No. 13/180,427, filed Jul. 11, 2011, and U.S. application Ser. No. 13/427,617, filed Mar. 22, 2012.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Intraocular implants such as an intraocular lens ("IOL") can be delivered into the eye through a small incision made in the cornea. Delivery devices have been developed to aid in the delivery and insertion of such implants into the eye.

A corneal or scleral incision allows access to the eye and the smaller the incision the less damage will be done and the less time will be needed for the incision to heal. In addition, the intraocular lens is preferably not damaged during delivery, or at most, minimally damaged such that it will not affect the functionality of the intraocular lens.

Depending on the physical characteristics of the intraocular lens (e.g., shape, size, etc.), the shape and/or configuration of the intraocular lens may need to be reduced in size or altered during the delivery process to enable the intraocular lens to be inserted through a small incision. The reduction in size or adjustment of the configuration/shape of the lens allows for a smaller delivery profile.

A delivery device is therefore needed that will reduce the delivery profile of the intraocular lens such that it can be delivered into the eye through a small incision. Additionally, the delivery device minimizes and preferably eliminates damage done to the lens during the delivery process, including the loading of the intraocular lens into the delivery device.

SUMMARY

One aspect of the invention is a method of hydraulically loading an intraocular lens into a delivery system. The method includes positioning an intraocular lens within a compression chamber and adjacent a delivery device, wherein the compression chamber and the delivery device are in fluid communication. The method includes flowing a fluid through the compression chamber and into the delivery device, wherein flowing the fluid through the compression chamber comprises loading the intraocular lens into the delivery device.

In some embodiments loading the intraocular lens into the delivery device comprises compressing the intraocular lens from an unstressed expanded configuration to a stressed delivery configuration. Compressing the intraocular lens can increase the length of the intraocular lens. The intraocular lens can comprise a fluid therein, and wherein compressing the intraocular lens comprises redistributing the fluid with the intraocular lens.

In some embodiments the intraocular lens comprises an optic portion, a first haptic, and a second haptic, and wherein positioning the intraocular lens within the compression chamber comprises positioning the first haptic distal to the optic portion.

One aspect of the invention is a hydraulic loading system for loading an ophthalmic device into a delivery device. The system includes a compression chamber with a tapered inner surface, wherein the compression chamber contains a fluid therein. The system includes a delivery device comprising an elongate loading element wherein the elongate loading element and the compression chamber are in fluid communication. The system includes an ophthalmic device disposed in a first configuration within the compression chamber. The system also includes a loading device adapted to cause the fluid to flow through the compression chamber and into the elongate loading element, thereby loading the ophthalmic device into the elongate loading element. In some embodiments the fluid contains a lubricant.

In some embodiments the ophthalmic device is an intraocular lens. In some embodiments the loading device comprises a plunger to direct the fluid through the compression chamber and into the elongate loading element.

One aspect of the invention is a method of loading an intraocular lens into a delivery device. The method comprises providing a delivery device comprising an everting tube comprising an inner tube portion and an outer tube portion, wherein the everting tube is coupled to a first actuation element. The method includes loading the intraocular lens into an end of the everting tube by actuating the first actuation element, wherein actuating the first actuation element everts a section of the outer tube portion into the inner tube portion about the end of the everting tube.

In some embodiments loading the intraocular lens into an end of the everting tube comprises compressing the intraocular lens within the inner tube portion. In some embodiments loading the intraocular lens into an end of the everting tube comprises loading a first haptic into the end of the everting tube before loading an optic portion of the intraocular lens. Loading the first haptic into the end of the everting tube can include forcing a volume of fluid from the first haptic into the optic portion.

In some embodiments loading the intraocular lens into an end of the delivery tube comprises engaging the intraocular lens and the inner tube portion, wherein the inner tube portion compresses the intraocular lens as the everting tube everts. In some embodiments actuating the first element moves the first actuation element in a proximal direction or a distal direction.

One aspect of the invention is a method of loading an intraocular lens into a delivery device. The method includes compressing an intraocular lens from a first configuration to a second configuration within a first portion of the delivery device, wherein compressing the intraocular lens comprises applying a compressive force to the intraocular lens in a direction generally orthogonal to a longitudinal axis of the delivery device. The method also includes actuating a second portion of the delivery device to move the second portion of the delivery device relative to the first portion of the delivery device in a direction generally parallel to the longitudinal axis of the delivery device, wherein actuating the second portion relative to the first portion loads the intraocular lens into the delivery device.

In some embodiments applying a compressive force to the intraocular lens comprises applying the compressive force indirectly to the first portion of the intraocular lens. In some embodiments applying a compressive force to the intraocular lens comprises applying the compressive force directly to a third portion of the intraocular lens, wherein the method further comprises engaging the third portion and the first portion.

In some embodiments the first portion and the second portion slidingly engage one another, and wherein actuating a second portion comprises sliding the second portion over the first portion. The delivery device can include a third portion engaging an outer surface of the first portion, and wherein sliding the second portion over the first portion displaces the third portion from the first portion.

In some embodiments compressing the intraocular lens within a first portion of the delivery device comprises moving a first half of the first portion closer to a second half of the first portion.

One aspect of the invention is a loading system for loading an intraocular lens into a delivery device. The system comprises an outer loading tube adapted to be inserted through an incision in the eye and an inner sleeve slidingly engaged with the outer loading tube and adapted to be disposed within the outer loading tube. The inner sleeve is adapted to engage an intraocular lens therein. The system includes a compressing member disposed adjacent an outer surface of the inner sleeve.

In some embodiments the inner sleeve comprises a first sleeve element and a second sleeve element, and wherein the first sleeve element and the second sleeve element are disposed apart from one another in a first configuration and are moved towards one another in a delivery configuration, thereby compressing the intraocular lens.

In some embodiments the compressing member comprises a first compressing element and a second compressing element, and the first compressing element engages an outer surface of the first sleeve element and the second compressing element engages an outer surface of the second sleeve element. The first compressing element and the second compressing element can be disposed apart from one another in a first configuration and are moved towards one another in a second configuration. The outer loading tube can be adapted to be actuated to displace the compressing member.

In some embodiments the outer loading tube is coupled to a loading tube actuator and the inner sleeve is coupled to an inner sleeve actuator, and wherein actuation of either the loading tube actuator or the inner sleeve actuator moves the outer loading tube relative to the inner sleeve.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention relates generally to delivery devices for delivering an intraocular implant, such as an IOL, through an incision in an eye. The delivery devices generally compress and increase the length of the IOL (or at least portions of the IOL) into a delivery configuration such that it can be delivered through a small incision, relative to the size of the IOL, into the eye. In addition, the delivery devices minimizes shear and tensile forces to the IOL during the delivery process to minimize and preferably eliminate damage to the IOL.

The IOLs described herein are accommodating IOLs implanted within a lens capsule after the native lens has been removed from the eye. In particular, the IOLs contain flowable media such as a fluid that is, in response to ciliary muscle movement, moved in the IOL to change the power of the IOL. Such exemplary IOLs are described more fully in U.S. Provisional Application No. 60/433,046, filed Dec. 12, 2002; U.S. Pat. Nos. 7,122,053; 7,261,737; 7,247,168; and 7,217,288; U.S. patent application Ser. No. 11/642,388, filed Dec. 19, 2006, now U.S. Pat. No. 8,361,145; and U.S. patent application Ser. No. 11/646,913, filed Dec. 27, 2006, now U.S. Pat. No. 7,637,947, the complete disclosures of which are hereby incorporated herein by reference. Is it also contemplated that the delivery devices described herein can, however, be used to deliver other types of accommodating IOLs (e.g., non fluid-driven accommodating IOLs), non-accommodating IOLs, and even other types of intraocular implants. In addition, it is contemplated that the delivery devices can be used to deliver the IOL or other ophthalmic device to portions of the eye other than within the lens capsule, such as the anterior chamber or to the posterior chamber after a lens capsule has been removed.

The delivery devices reduce the delivery profile of the IOL by compressing the IOL, or portions of the IOL, from an expanded configuration to a delivery configuration. In some embodiments the IOL assumes a generally circular shape before being loaded of the delivery device, but is compressed into a lengthened generally cylindrical shape by the delivery device. One advantage of the delivery devices is that they minimize the amount and/or types of forces acting on the IOL during the delivery procedure (including the loading and deployment), which can help minimize the amount of damage to the IOL during delivery. This can be advantageous for delicate IOLs (comprised, for example, of polyermic materials) and/or IOLs which comprise a plurality of interconnected components, the mating or bonded elements of which can be damaged by certain types of forces acting on the IOL during a loading and deployment procedure.

In preferred embodiments, the delivery devices minimize shear and tensile forces on the IOL during the delivery process, and instead reshape the IOL under compression.

Figure 1A:
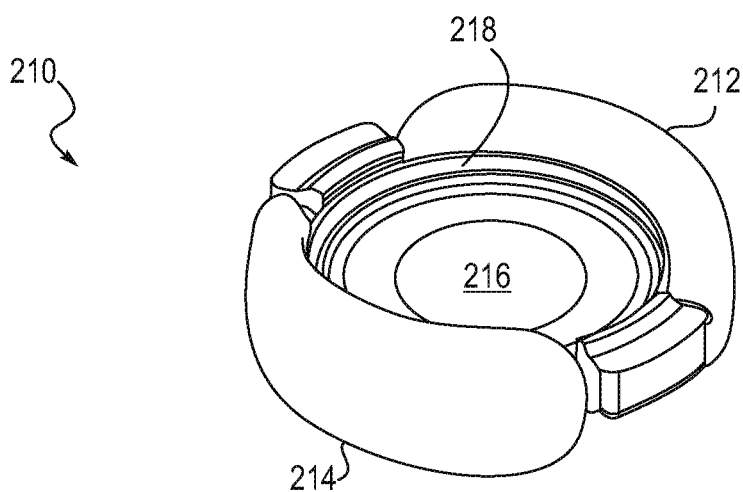
FIGS. 1A, 1B and 1C illustrate an exemplary fluid-driven accommodating intraocular lens.
Figure 1B:
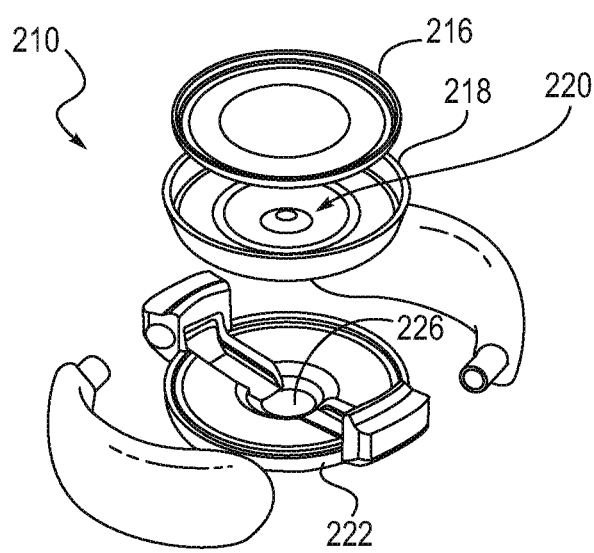
Figure 1C:
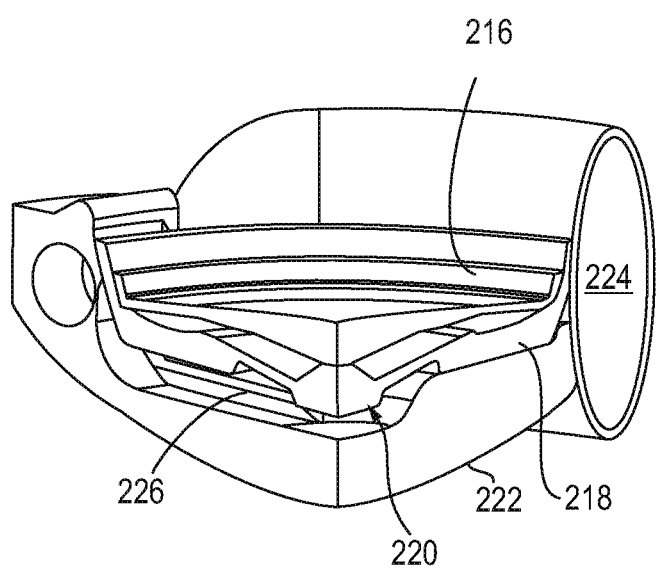

FIGS. 1A-1C illustrate an exemplary fluid-driven accommodating IOL 210 that can be delivered within the lens capsule with the delivery devices described herein. IOL 210 includes a non-option peripheral portion which includes haptics 212 and 214. IOL 10 also includes an option portion which includes anterior element 216, intermediate layer 218, and posterior element, or substrate, 222. Intermediate layer 218 includes actuator 220. Haptics 212 and 214 define interior volumes 224 which are in fluid communication with active channel 226 defined by posterior element 222 and intermediate layer 218. The haptics engage the capsular bag such that zonule relaxation and tightening causes deformation of the haptics, which distributes a fluid disposed in the haptics and active channel between the haptics and the active channel. When fluid is directed from the haptics to the active channel, the pressure increase in the active channel deflects actuator 220 in the anterior direction, causing the curvature of anterior element 216 to become steeper. This increases the power of the IOL. This process is described in more detail in any of the exemplary patent applications and patents listed above.

Figure 2:
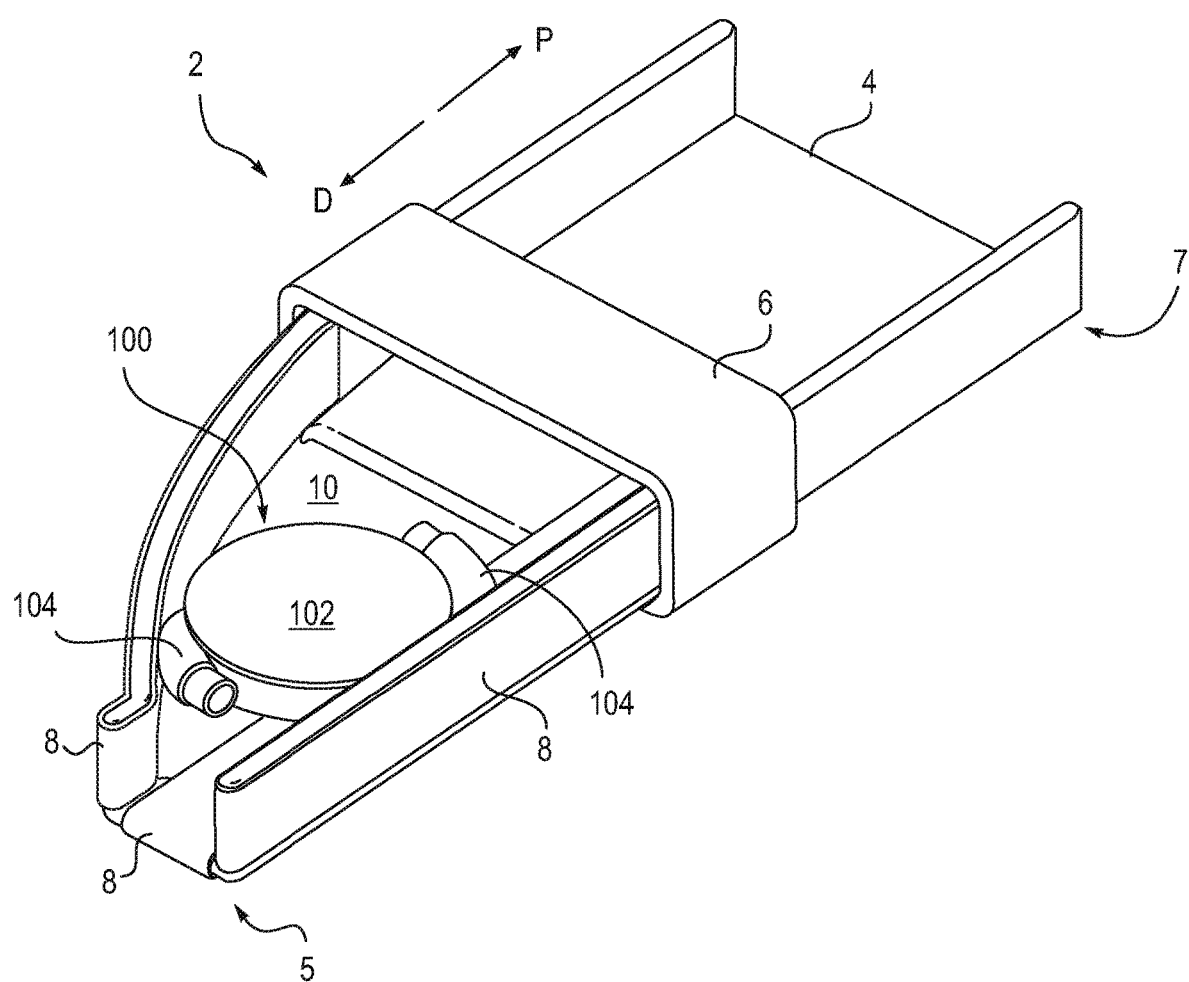
FIGS. 2 and 3 show an exemplary delivery device.

FIG. 2 illustrates an exemplary embodiment of delivery device 2 and IOL 100. IOL 100 comprises optic portion 102 and haptics 104 (see FIG. 3) positioned within the delivery device in an unstressed, or expanded, configuration. Delivery device 2 includes inserter body 4, pull block 6, and belts 8. The pull block is connected to the belts on the belt portions that are on the exterior surfaces and bottom surface of the inserter body (bottom not shown), but is not connected to the belts on the inside of the inserter body. Movement of the pull block in either of the direction of arrows D and P moves the portion of the belts on the inside of the inserter body to move in the direction generally opposite the direction of movement of the pull block. For example, when pull block 6 is moved in the proximal, or P direction, the belt portions on the interior of the body move generally in the D direction. The belts act generally as conveyor belts to move the IOL the pull block is actuated.

In use, when the pull block is pulled in the proximal direction (the direction of arrow P in FIG. 2), this causes the portion of the belts on the inside of the inserter body to move in the general distal direction (the direction of arrow D) along the interior surfaces of the inserter body. The belts on the outside and bottom of the inserter body move in the proximal direction as well. As the portion of the belts on the inside of the inserter body move distally, they eventually move around distal end 5 of the inserter body to the outside of the inserter body.

Similarly, when the pull block is pushed distally, or in direction D, the portion of the belts on the outside and bottom of the inserter body move distally and the portion of the belts on the inside of the inserter body move proximally. This causes the IOL in the inside of the body to move in the proximal direction.

The delivery device is configured so that only the belts and not the inserter body (or as little of the inserter body as possible) engage the IOL. Because the IOL does not make contact with the inserter body (or any other parts of the delivery device that may be added), the inserter body does not apply tensile force or shear forces/stress on the IOL as the IOL is moved by the belts. In addition, because the belts move with the IOL, the amount of shear and tensile forces applied to the IOL by the belts are minimized. As shown in FIG. 2, there is an opening or space 10 formed in the bottom surface of the inserter body. The opening in the inserter body is created to avoid contact between the inserter body and the IOL to help minimize unwanted forces on the IOL.

To deliver the IOL into the eye, the IOL is positioned in the interior of the inserter body, making contact with substantially only the belts. The IOL is positioned in an expanded configuration so it is just barely making contact with the belts (as shown in FIG. 2). The pull block is actuated in the proximal direction and the IOL is moved in the distal direction towards the distal end 5 of the device. Because of the reduced width of the distal end of the device compared to proximal end 7, the IOL is compressed as it moves distally and then passes out of distal end 5. It is delivered from the distal end of the device into the eye, where it expands after being released from the delivery device.

When compressing a closed-system fluid-filled IOL (as is shown in 1A-1C and in FIG. 2) in the conveyor system, the portion of the IOL nearest to distal end 5 of inserter body 4 will begin to compress before the rest of the IOL. As the distal end of the IOL begins to compress, fluid contained within the IOL will generally be squeezed or forced into more proximally positioned portions of the IOL. In addition, the first portion of the IOL to be deployed from the delivery device will begin to expand, and while more proximal portions of the IOL continue to be compressed, some fluid will begin to be squeezed distally into the now free and expanding distal portion of the IOL.

Figure 3:
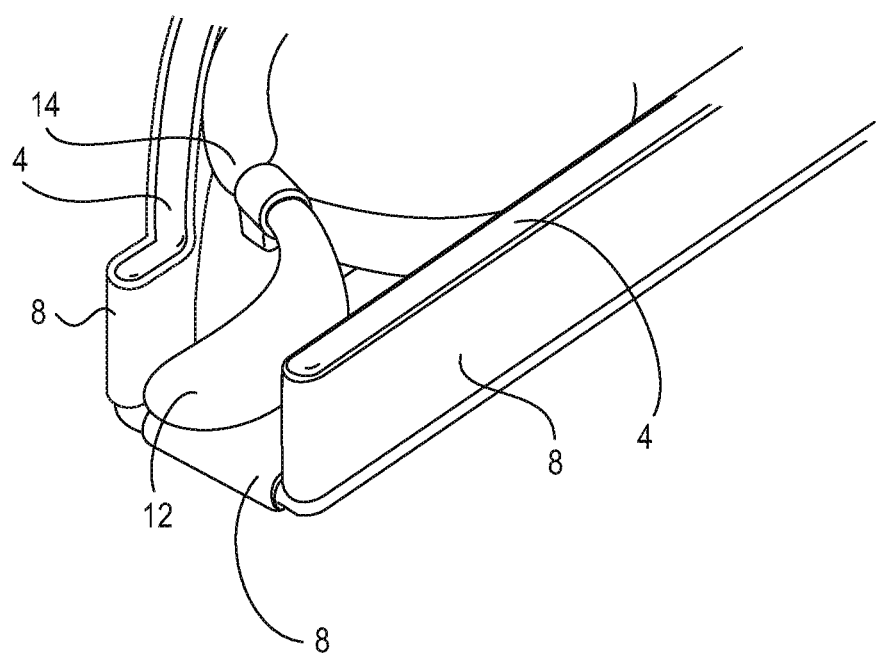

It may therefore be advantageous to orient the IOL in the inserter body prior to compression such that fluid will be distributed throughout the IOL in a predictable manner to enable compression and minimize damage to the IOL. For example, FIG. 3 shows distal end 5 of the inserter body in more detail. The IOL is positioned in the inserter body so that a leading (or distal) haptic 12 begins to be deployed first from the inserter body. When the leading haptic begins to be released from the inserter body, the leading haptic can receive fluid that is squeezed from the optic portion and/or trailing haptic 14.

This embodiment may require high tensile forces on the belts, so a pulling mechanism would preferably utilize features designed to increase mechanical advantage. Levers, screws, and/or ratchets could be used to give a user the control as well as the required force.

The inserter body is generally a rigid structure with a general tapered shape with the width decreasing towards the distal end to compress the IOL as it is moved in the distal direction. In some embodiments the distal end of the inserter body is less than about 50% of the width of the proximal end. This is not intended to be a limitation and may be less than about 40%, about 30%, about 20%, about 10%, or less, than the width of the proximal section. While the embodiment shown only includes a bottom surface, the inserter body could also have a top surface (with a similar space as in the bottom surface to avoid sliding). If the inserter body did have a top surface, a fourth belt could then also be included in the device.

The pull block and belts can be made of a relatively rigid material such as Mylar or an elastomeric material such as a silicone.

While three belts are shown in this embodiment there may be more, such as 4, or fewer in the delivery device.

Figure 4:
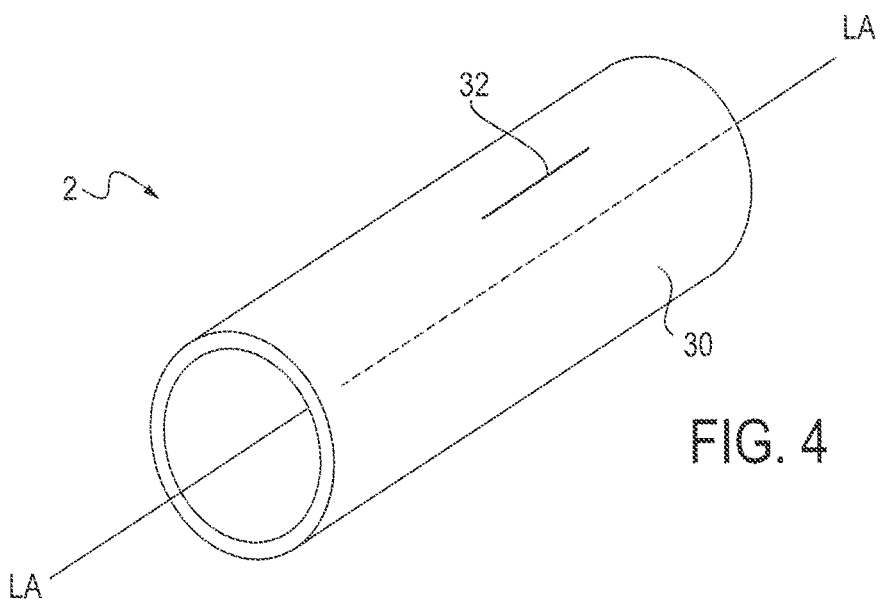
FIGS. 4, 5, 6, 7 and 8 illustrate an exemplary embodiment of an everting tube with a slit therein.

FIG. 4 illustrates a second embodiment of a delivery device. In this embodiment the delivery device comprises an everting tube 30 that includes at least one slit or cut 32 along at least a portion of the length of the tube. The term everting as used herein generally means that at least one section of the tube is adapted to roll back or fold back onto the tube, like a pair of socks or the cuff on a pair of pants. In some embodiments, however, the everting tube does not have a slit.

Everting as used herein can refer both to the step when the inner surface of the tube rolls outward and back and becomes an outer surface of the tube, or when an outer surface of the tube rolls inward and becomes an inner surface.

FIG. 4 shows everting tube 30 in a non-everted state (no section of tube is everted, or rolled back). Slit 32 is shown running parallel to the longitudinal axis LA of the tube 30.

Figure 5:
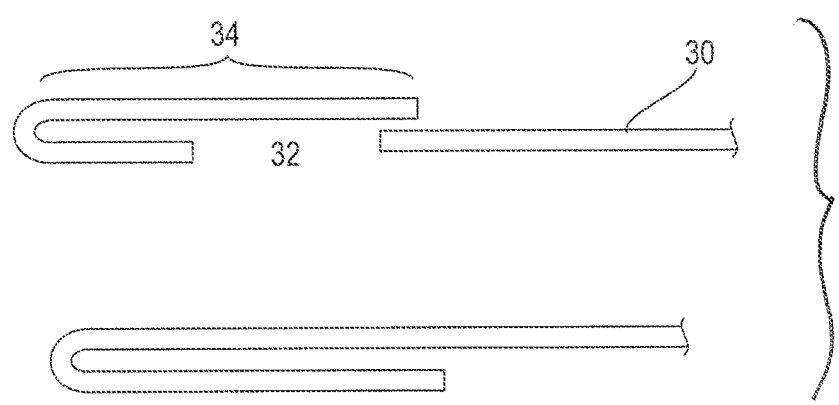

FIG. 5 is a cross sectional view of the tube with a distal portion 34 everted, however the portion of the tube including slit 32 has not yet been everted.

Figure 6:
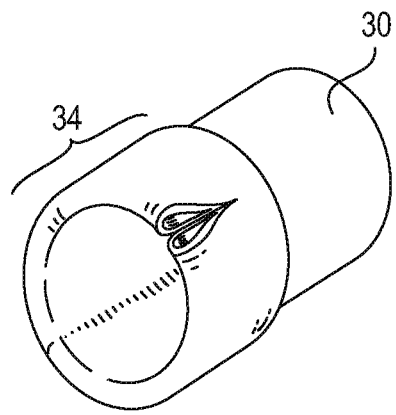
Figure 7:
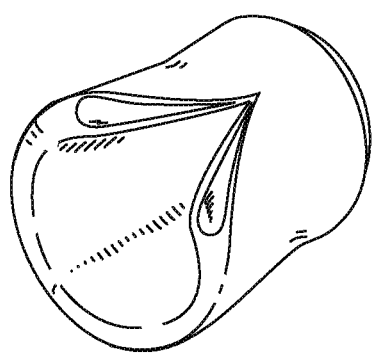
Figure 8:
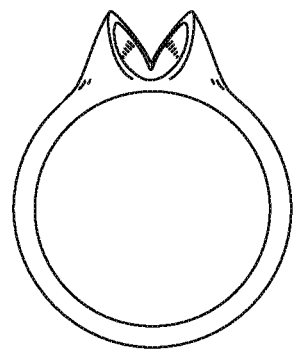

FIG. 6 shows a perspective view of an exemplary everting tube 30 as the portion of the tube including the slit has begun to evert. The slit in the tube causes the portion of the tube circumferentially surrounding the slit to "blossom" as the distal end of the slit reaches the distal end of the tube and as the portion of the tube circumferentially surrounding the slit begins, and continues, to evert. FIG. 7 shows the slit continuing to blossom. FIG. 8 is a distal end view of the slit blossomed. Once the slit portion of the tube is fully everted, the remainder of the tube continues to evert in the same manner as did the portion of tube disposed proximally to the slit. It is in this manner that the slit in the tube allows for a greater expansion or opening of the tube as it is everted.

Figure 9:
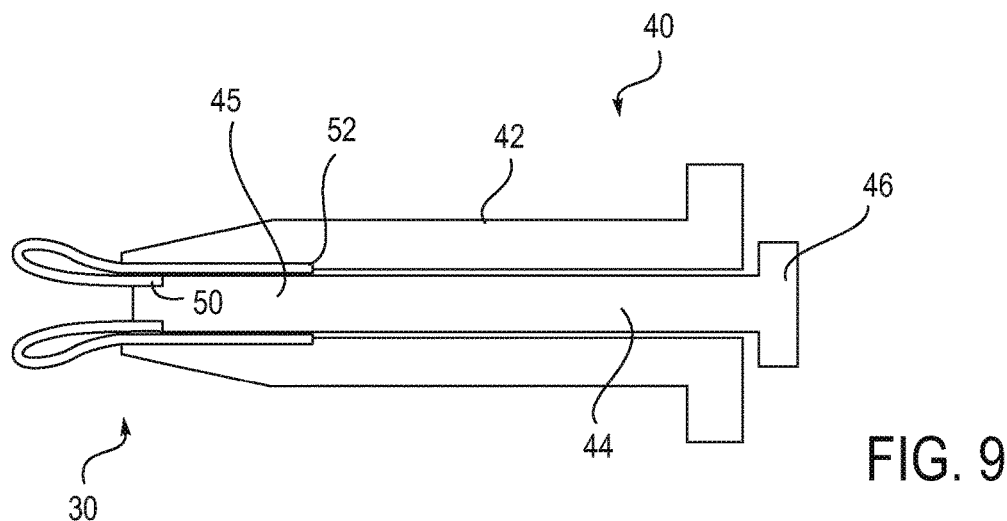
FIGS. 9 and 10 illustrate an exemplary delivery device incorporating an everting tube.

In one embodiment of the everting tube concept as shown in FIG. 9, the everting tube is coupled to a syringe-like device 40. Device 40 includes an outer body 42 comprising an inner bore or channel through which inner body 44 passes. Inner body 44 includes handle 46 at its proximal end. The proximal end 50 of everting tube 30 is coupled to distal portion 45 of inner body 44 and distal end 52 of the everting tube 30 is coupled to outer body 42. When inner body 44 is actuated in the distal direction (e.g., by pushing handle 46 distally), inner body 44 moves distally relative to outer body 42. Because the proximal end of the everting tube is coupled to distal portion 45 of the inner tube, this movement also moves the proximal portion of the everting tube in the distal direction. Distal end 52 of the everting tube remains coupled to outer body 42 and thus does not move. Similarly, when the inner body is moved or pulled proximally, such as by pulling on the handle in the proximal direction (or otherwise actuating inner body 44), inner body 44 moves proximally relative to outer body 42 and therefore so does the proximal end of the everting tube. It is noted that it is the relative movement of the inner and outer bodies that controls the movement (and thus the everting) of the everting tube, and the outer body can similarly be advanced in the distal direction or retracted in the proximal direction over the inner body to cause the relative movement.

In addition the inner and outer bodies may be disposed within an outer sheath such that the user of the delivery device would not see the inner and outer bodies. The inner and outer bodies could also be coupled to an actuator such as a control knob which a user could use to carefully control the advancement of the inner body relative to the outer body or the retraction of the outer body relative to the inner body. This could give the user precise control over the delivery of the IOL.

To deliver an IOL into the eye, an IOL is first loaded into the distal end of the delivery device shown in FIG. 9 as follows. Handle 46 is advanced distally (or a knob is rotated, or other actuator to control the relative movement of the inner and outer bodies) as shown in FIG. 9 such that a portion of the everting tube is disposed outside and distal to outer body 42. The slit in the everting tube is exposed, or outside of the outer body, and has "bloomed." The IOL is placed into the blooming opening and the handle is then actuated in the proximal direction, or the outer body is advanced in the distal direction, or both. As the inner layer of the everting tube moves in the proximal direction, causing more of the outer layer of the tube to roll inward and become part of the inner layer of the tube, the slit is retracted within the outer layer of the tube. The slit is thereby forced closed and the device is compressed in the tube via the hoop forces on the closed, or intact, portion of the tube.

Because the tube is everting inward and moving with the IOL (similar to the belts in the embodiment shown in FIGS. 2 and 3), the amount of shear and tensile forces on the IOL are minimized. Substantially all of the sliding (and accompanying shear forces) occurs between the two layers of the everting tube, so there is no (or very little) sliding between the everting tube and the IOL. In some embodiments a lubricant is applied to the everting tube to minimize shear and forces.

As the handle continues to be pulled in the proximal direction, the IOL continues to be loaded into the outer body as the IOL moves further proximally into the channel. In this embodiment, the compression is accomplished as the hoop forces force the IOL to be compressed as it is drawn into the everting tube.

Figure 10:
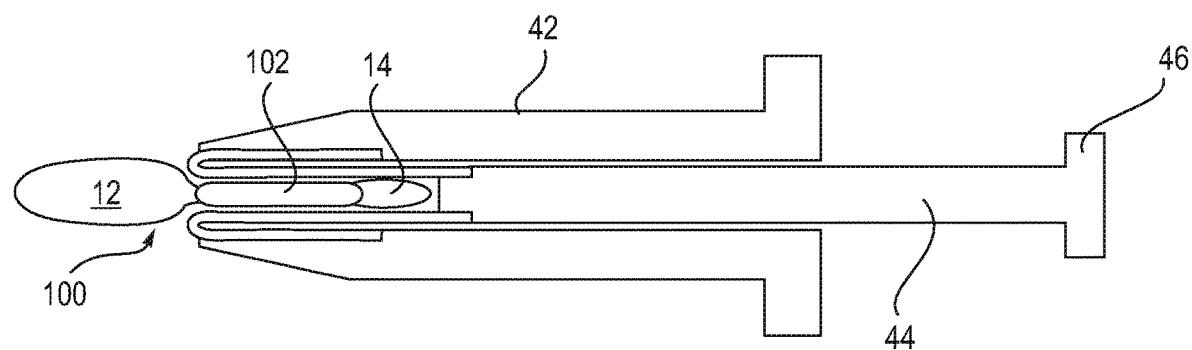

FIG. 10 shows a cross sectional view of an exemplary IOL 100 with a portion of the IOL loaded into the delivery device (and within the everting tube), as described by the loading process above. The exemplary IOL 100 is a soft, flexible, accommodating IOL which includes an optic portion 102 and a peripheral portion comprising haptics 12 and 14 in fluid communication with the optic portion. The IOL comprises fluid which is transferred between the haptics and optic portion to accommodate the IOL in response to ciliary muscle movement.

When compressed into the delivery configuration, the length of IOL 100 increases (as is shown in FIG. 10) while the IOL narrows. When compressed, the fluid within the IOL is squeezed from the portion of the IOL loaded first. As shown in FIG. 10, proximal, or trailing, haptic 14 is loaded first, which squeezes the fluid from the proximal haptic into the optic portion (and likely into distal haptic 12 as well). As the optic portion is loaded into the delivery device (e.g., as the handle continues to be pulled proximally), the optic portion is compressed by the everting tube and the fluid in the optic portion is squeezed into the distal haptic 12.

FIG. 10 shows the IOL in the loaded, or delivery, configuration. Distal haptic 12 is external to the delivery device and contains a larger volume of fluid that it contains when the IOL is in an expanded configuration. Similarly, optic portion 102 and trailing haptic 14 contain less fluid than they do when in an expanded configuration. In this delivery configuration, the IOL has been partially compressed and elongated, and much of the fluid has been squeezed into the distal, or leading, haptic.

To deploy the IOL into the eye (e.g., into the lens capsule of which the native lens has been removed), the distal, or leading, haptic is pushed through the corneal incision and into the capsule. Then inner body 42 is pushed distally (or the outer body is pulled proximally, or both), which causes the everting tube and the loaded IOL to move distally together, deploying the IOL from the delivery device and into the eye by squeezing out through the blooming slit portion of the everting tube. As the optic portion of the IOL begins to be released from the outer body, the fluid moves from the distal haptic to the optic portion, causing the optic portion to expand in volume. Then, as the proximal haptic is released from the delivery device it begins to refill with fluid and increases in volume. Once the IOL has completely been deployed outside of the delivery device (and into the capsule), the IOL has generally returned to its pre-loaded, generally expanded, configuration (although the shape of the IOL may be slightly altered after implantation due to forces acting on the IOL by the lens capsule). The delivery device is then removed from the eye.

Figure 11A:
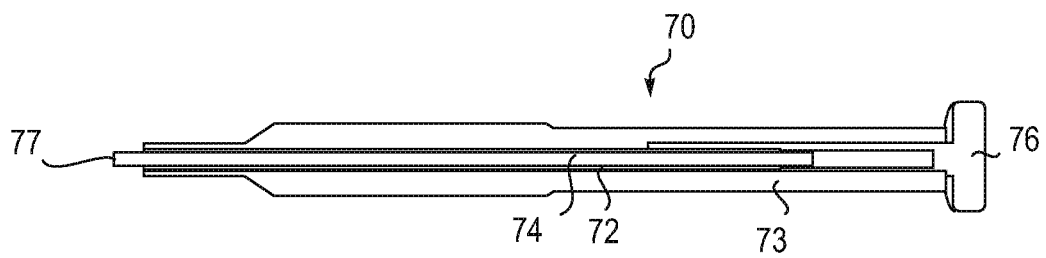
FIGS. 11A, 11B, 11C and 11D show an exemplary delivery device incorporating an everting tube.
Figure 11B:
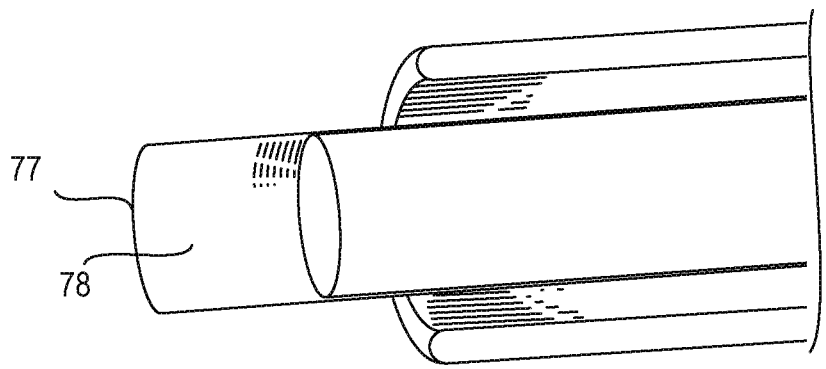
Figure 11C:
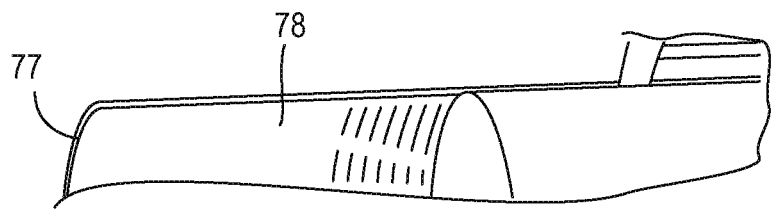
Figure 11D:
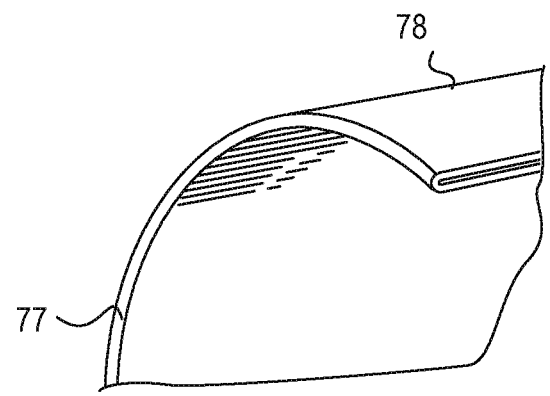

FIGS. 11A-11D show an alternative embodiment of delivery device 70 comprising outer body 72 and inner body 74 with knob 76. To load the IOL, knob 76 is rotated which actuates inner body 74 in the proximal direction and/or actuates the outer body in the distal direction. To deploy the IOL, the knob 76 is rotated which actuates the inner body in the distal direction and/or actuates the outer body 72 in the proximal direction. Sheath 73 covers outer body 72 and provides the surgeon a stable handle with which to work. FIG. 11D shows a close-up perspective view of distal end 77 of everting tube 78.

In the embodiments shown in FIGS. 11A-11D, distal end 77 of the everting tube can be adapted such that it does not move relative to the eye during the implantation procedure. The tube will evert (the inner tube become outer tube, or the outer tube becomes inner tube), however the distal end remains substantially fixed in space. This is important because the user does not have to worry about distal end 77 contacting and disrupting the eye during the procedure. The user also does not have to worry about moving the distal end of the delivery system relative to the eye during the deployment procedure.

Figure 12A:
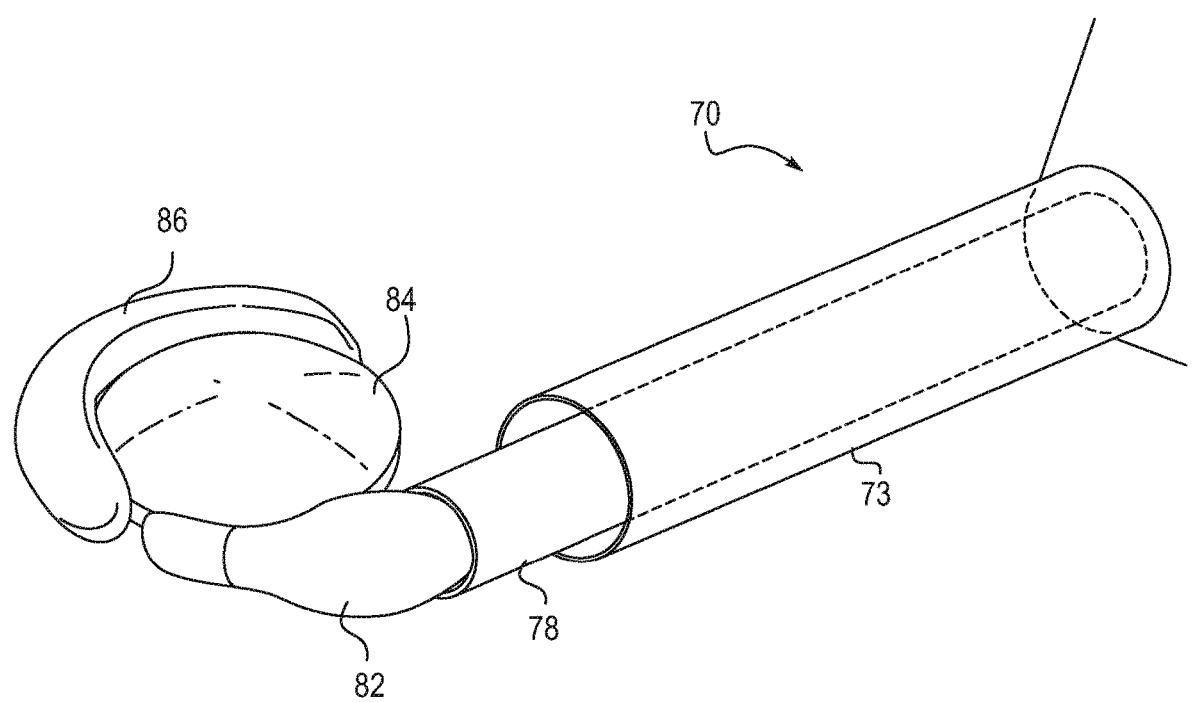
FIGS. 12A, 12B and 12C illustrate the loading of an exemplary intraocular lens in a delivery device.
Figure 12B:
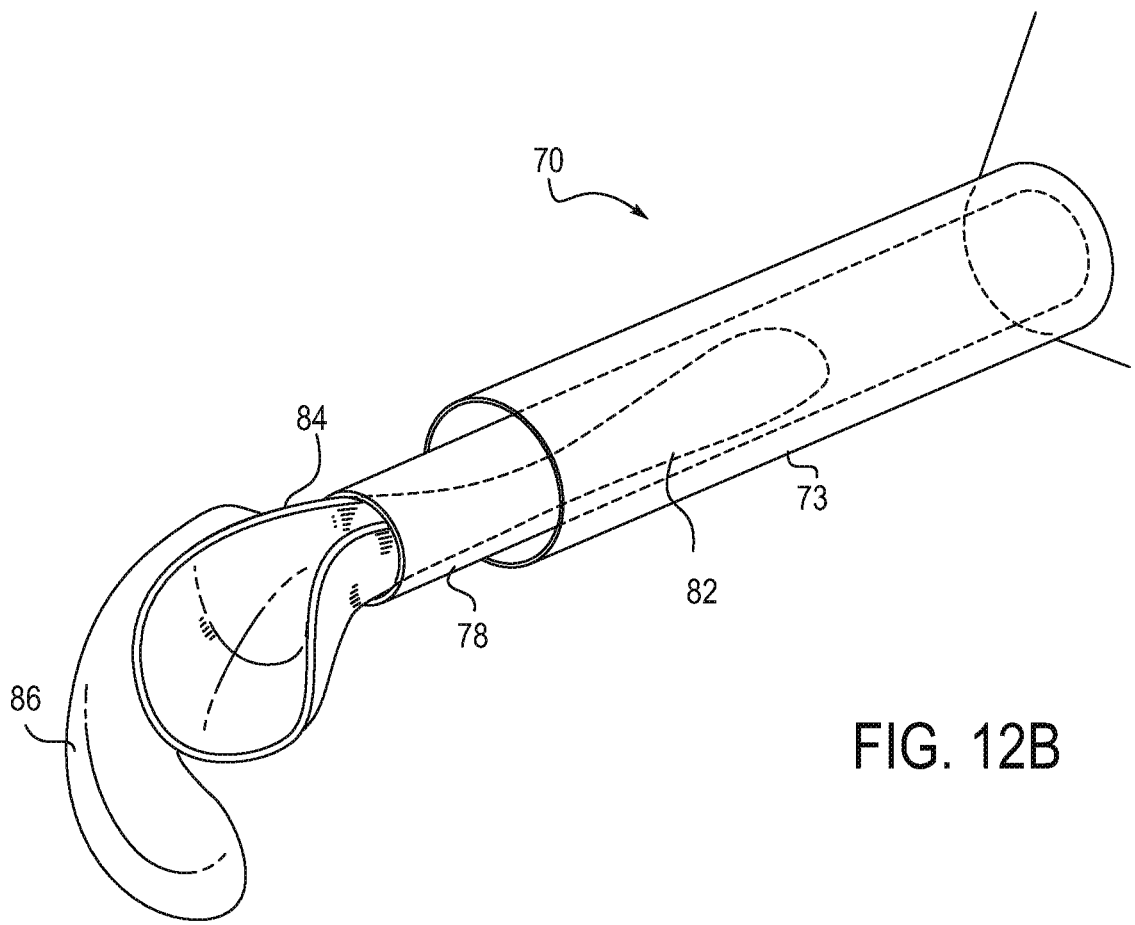
Figure 12C:
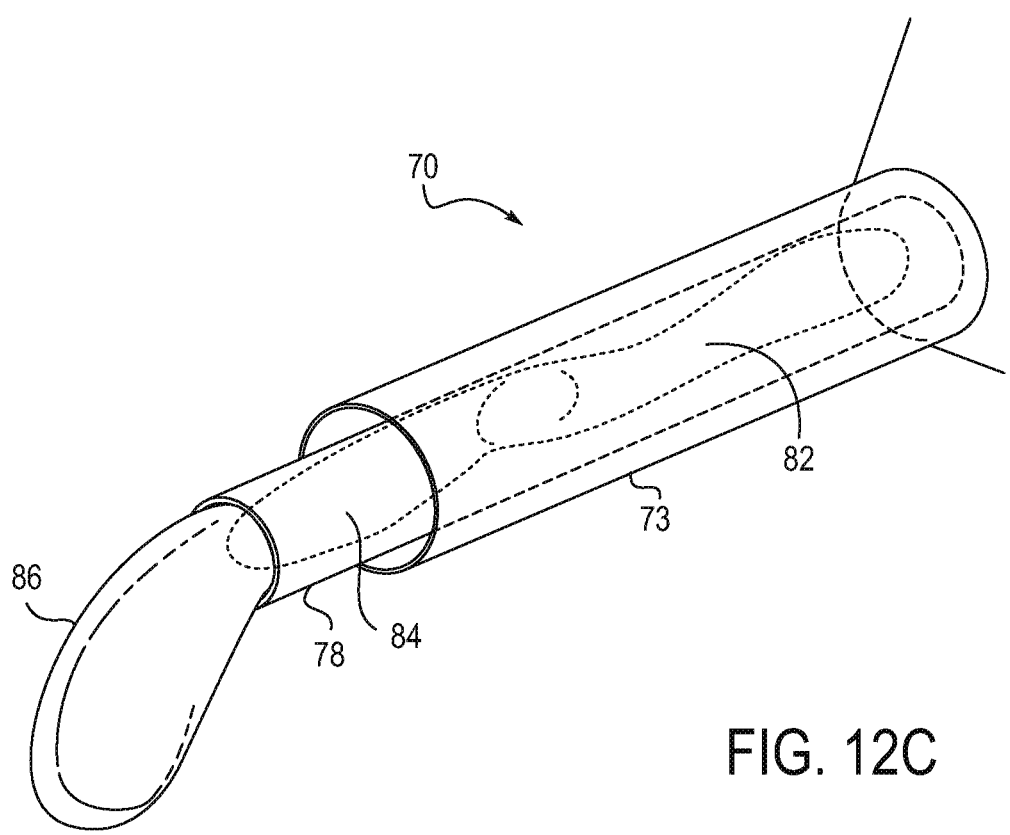

FIGS. 12A-12C show the loading of IOL 80 into delivery device 70 as described above. IOL 80 comprises trailing haptic 82, optic portion 84, and leading haptic 86. Delivery of the IOL into an eye occurs in the reverse order of the steps shown in FIGS. 12A-12C.

Figure 13A:
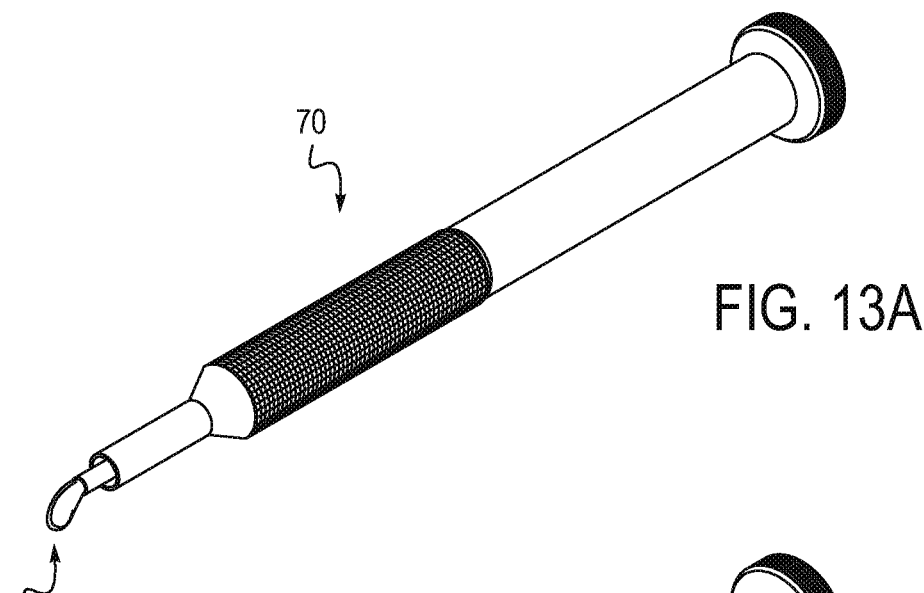
FIGS. 13A, 13B and 13C illustrate the deploying of an exemplary intraocular lens from a delivery device.
Figure 13B:
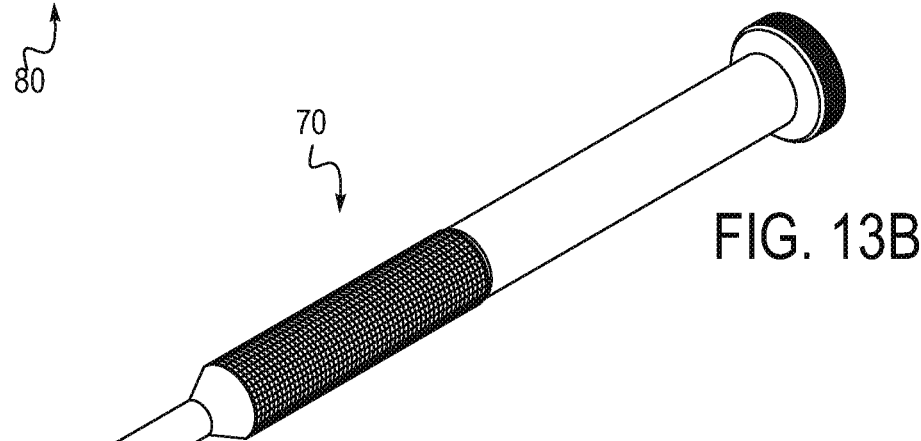
Figure 13C:
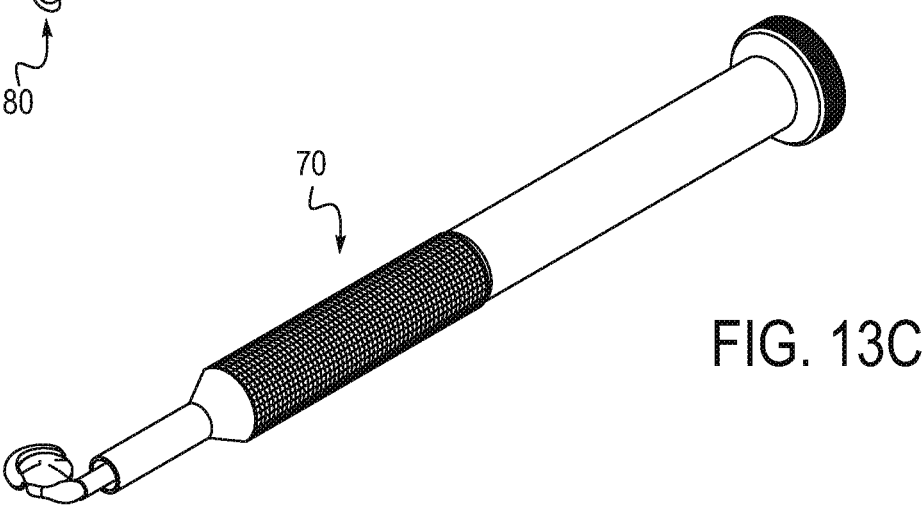
Figure 14:
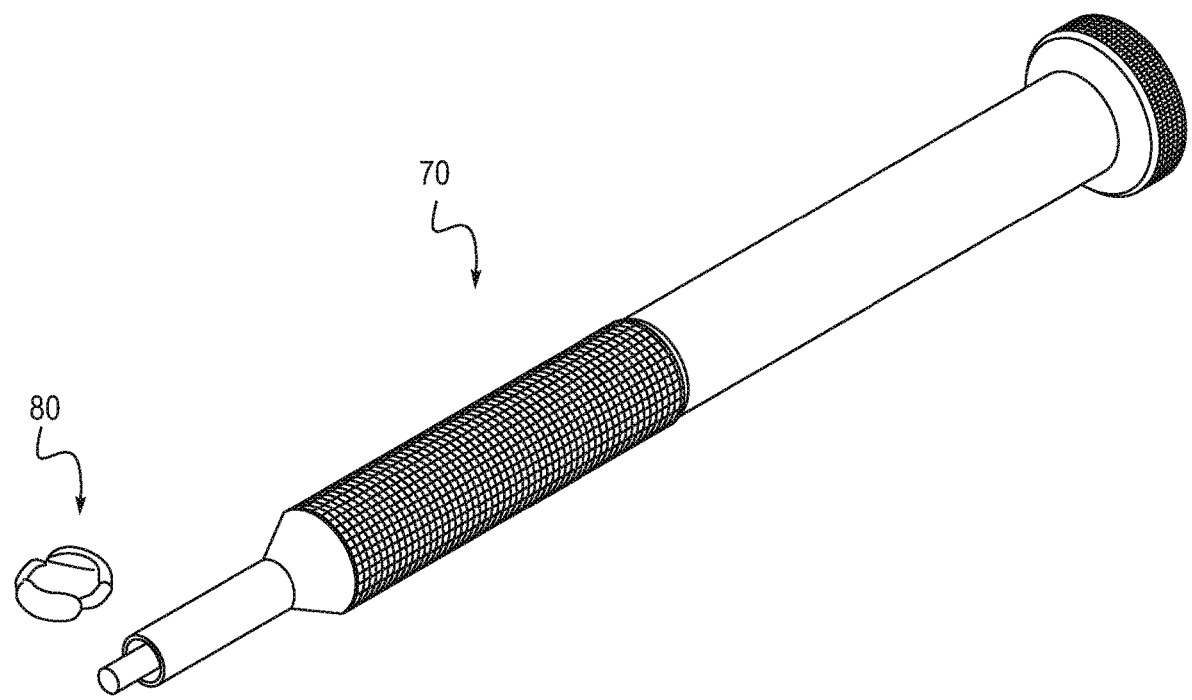
FIG. 14 illustrates an exemplary delivery device relative to an exemplary intraocular lens.

FIGS. 13A-13C show deployment of IOL from delivery device 70. FIG. 13A shows a leading haptic extending from the distal end of the everting tube. FIG. 13B shows the optic portion emerging, and FIG. 13C shows the trailing haptic almost completely deployed. FIG. 14 illustrates the size of delivery device 70 next to IOL 80.

In some embodiments the everting tube is a thin, tough, generally stretchy material that is adapted to be everted. To evert a tube it is generally preferred to be somewhat stretchy and very thin relative to the inner diameter of the tube. A composite material with relatively different axial and circumferential stiffnesses may also be used. For instance, a tube can contain fibers running along the longitudinal axis of the tube that serve to stiffen the tube in the axial direction while maintaining the elastic properties in the circumferential direction. Alternatively, the everting tube can be formed by being drawn to provide extra stiffness along its length.

While the embodiments above show and describe one slit in the everting tube, the delivery device may have more than one slit, such as 2, 3, 4, 5, or more slits. The slits may be positioned around and along the length of the tube in any orientation that helps minimize the shear and tensile forces on the IOL during loading or deployment. In some embodiments the everting tube has no slits.

A variety of actuation mechanisms may be used to deliver the device. For example without limitation, a knob, a trigger, or a lever mounted on a grip may be used as alternatives to the syringe design.

Figure 15:
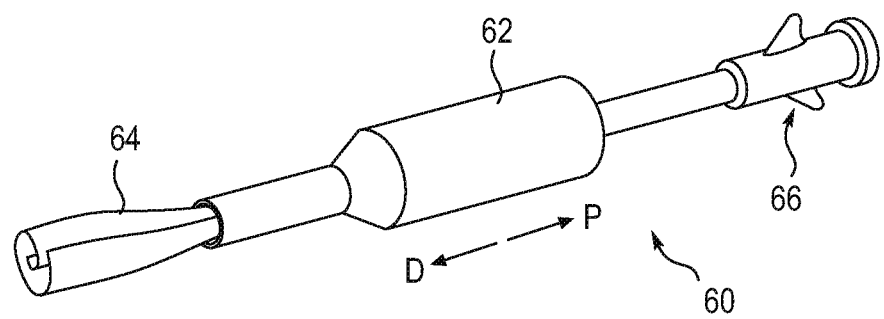
FIGS. 15, 16 and 17 illustrate an alternative delivery device.
Figure 16:
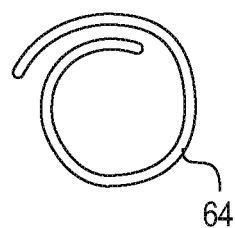

FIG. 15 illustrates an alternative delivery device 60 which comprises body 62, inserter 64, and advancement mechanism, or actuator, 66, which is coupled to inserter 64. Inserter 64 is a sheet that is rolled up along its length wherein one edge of the inserter overlaps the other, as shown in FIG. 16. The proximal end (not shown) of inserter 64 is coupled to the distal end (not shown) of advancement mechanism 66. As advancement mechanism 66 is actuated in the proximal direction, inserter 64 is withdrawn into body 62. Body 62 generally compresses inserter 64 when inserter 64 is withdrawn in to body 62. This causes the diameter of inserter 64 to decrease and the sheet forms a tighter roll or curl.

Figure 17:
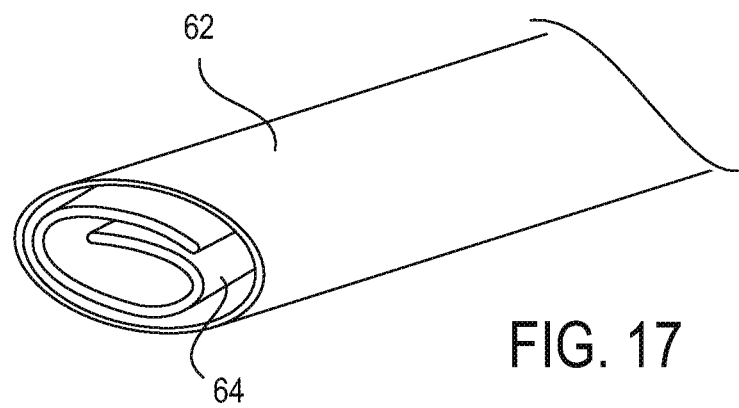

FIG. 16 is a distal end view of the inserter and FIG. 17 shows a perspective view of a distal end of body 62 with inserter 64 withdrawn into body 62.

To load the IOL into the delivery device 60, the advancement mechanism is pushed distally to deploy inserter 64 from the distal end of body 62 (as shown in FIG. 15). The distal end of the inserter body will assume a more open (i.e., the curl is not as tight), or first, configuration, allowing the IOL to be positioned in the distal end of the inserter. After placement of the IOL in the distal opening of the inserter, the advancement mechanism is pulled proximally (or body 62 is pushed distally). This pulls the inserter into body 62 whereby the body 62 exerts a compressive force on the inserter, causing it to fold more tightly into itself. The inserter thus applies a compressive force to the IOL. As in the other embodiments above, because the IOL moves proximally with the inserter, it is compressed within the inserter. The inserter and IOL move together and therefore shear and tensile forces acting on the IOL are minimized.

Once loaded into the delivery device, the IOL can then be inserted through the wound as described above.

Once body 62 has been advanced into the wound advancement mechanism 66 is advanced distally, which begins to deploy the folded inserter from the body. The IOL moves with the inserter as it is advanced out of body 62. As the inserter is pushed from body 62, it begins to unroll, or open, allowing the optic and trailing haptic to begin to expand and again fill with fluid that had been squeezed into the leading haptic when the IOL was in the loaded delivery configuration.

This embodiment may be used with an additional secondary advancement mechanism to further advance the IOL from the rolled inserter. For example, a plunger-like device could be disposed within an internal bore or channel in the advancement mechanism. The plunger-like device could be pushed distally through the advancement mechanism to make contact with the IOL to completely deploy the IOL from the folded inserter. Because the IOL might be in a generally uncompressed state after the inserter has been pushed as far distally as possible, only a small amount of additional force may be needed to completely push the IOL from the folded inserter. Therefore the plunger-like device would not damage the IOL.

An alternative secondary advancement mechanism uses a hydraulic force to fully deploy the IOL from the folder inserter. A lumen within the advancement mechanism can be used to deliver fluid within the inserter thereby forcing the IOL out of the inserter. Fluid will also minimize the amount of shear or tensile forces acting on the IOL. A sealing mechanism such as a plug or other insert (such as a silicone material) can also be positioned into the rolled inserter to help create a seal between the IOL and the inserter to aid in the hydraulic ejection of the IOL.

In general the rolled inserter is a very thin material. In one embodiment the rolled inserter comprises Mylar and is about 0.004" thick. The cross section of the inserter may assume a variety of cross-sectional shapes, such as round, oval, or elliptical.

FIGS. 18A-18E illustrate an embodiment of loading and delivery system 300 for loading and delivering intraocular lens 310. The system includes rigid outer tube 302, flexible inner sleeve 304 (split into two halves as shown), and compressor clips 306. Outer tube 302 is adapted to fit through about a 4 mm incision in the eye. Outer tube 302 is coupled to outer tube actuator 322 and inner sleeve 304 is coupled to inner sleeve actuator 324. The outer tube and inner sleeve can axially move with respect to one another by actuation of one or both of outer sleeve actuator 322 and inner sleeve actuator 324. The compressor clips can be lightly bonded (e.g., using a weak bonding material such as Loctite 495) or unbonded to the inner sleeve.

Figure 18A:
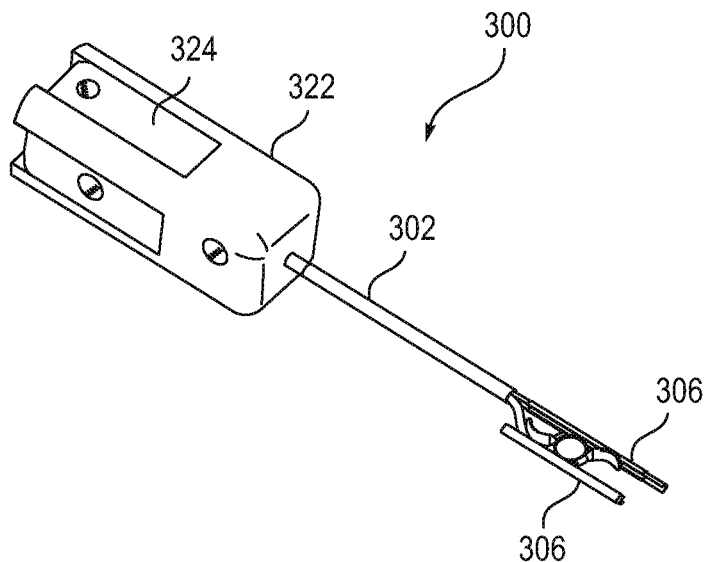
FIGS. 18A, 18B, 18C, 18D and 18E illustrate an alternative delivery device.
Figure 18B:
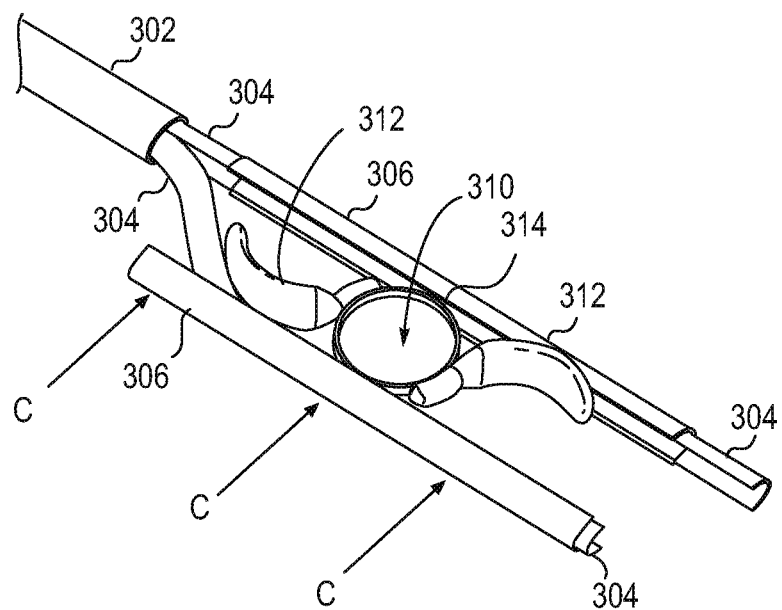

To load lens 310 into outer tube 302, the intraocular lens is first positioned in the system as shown in FIG. 18A (also shown in more detail in FIG. 18B). Haptics 312 are first positioned axially from optic portion 314 (one haptic leading and the other haptic trailing). This assists in the loading process. A compressive force in the general direction of arrows C is then applied to one or both of compressor clips 306. The compressive force can be applied by a vise or other similar device that brings two elements together to cause compressive force C to be applied to the compressor clips. As a result, a compressive force is applied to the lens and causes the lens to be compressed between the two halves of the inner sleeve. The inner sleeves, and not the compressor clips, engage the lens. The compressive force is applied until the two halves of the inner sleeve come together such that the lens is fully compressed within the two halves of the inner sleeve. The compressor clips can be compressed until they engage with each other or there may be a slight space between the edges of the compressor clips. During the compression process the lens is compressed and elongated.

Figure 18C:
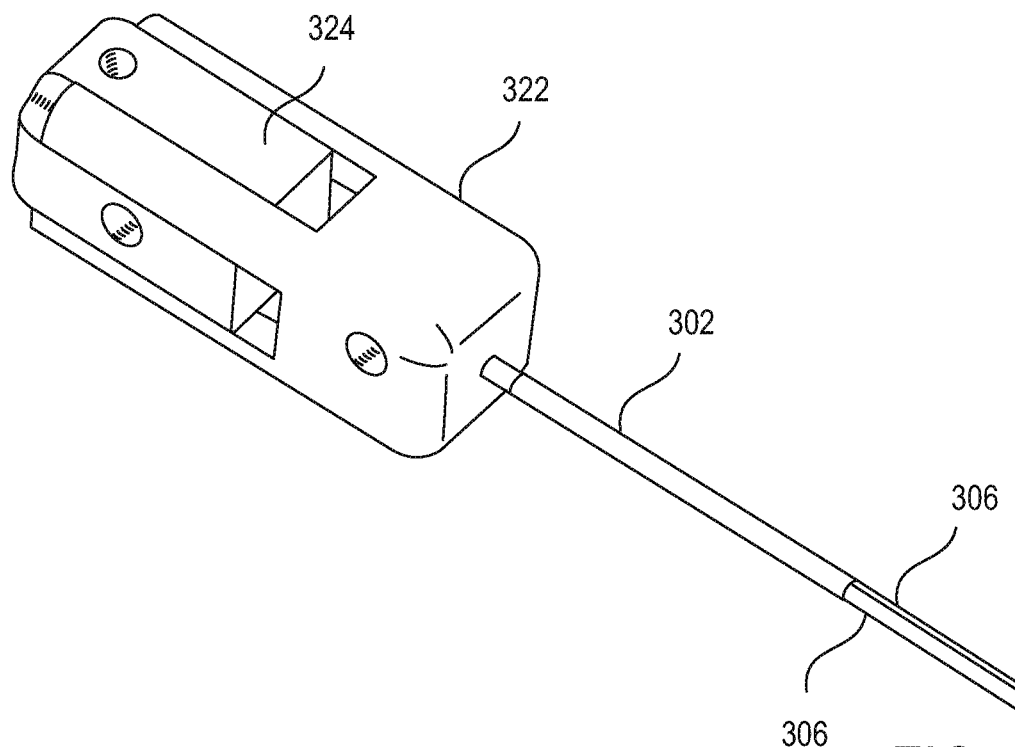
Figure 18D:
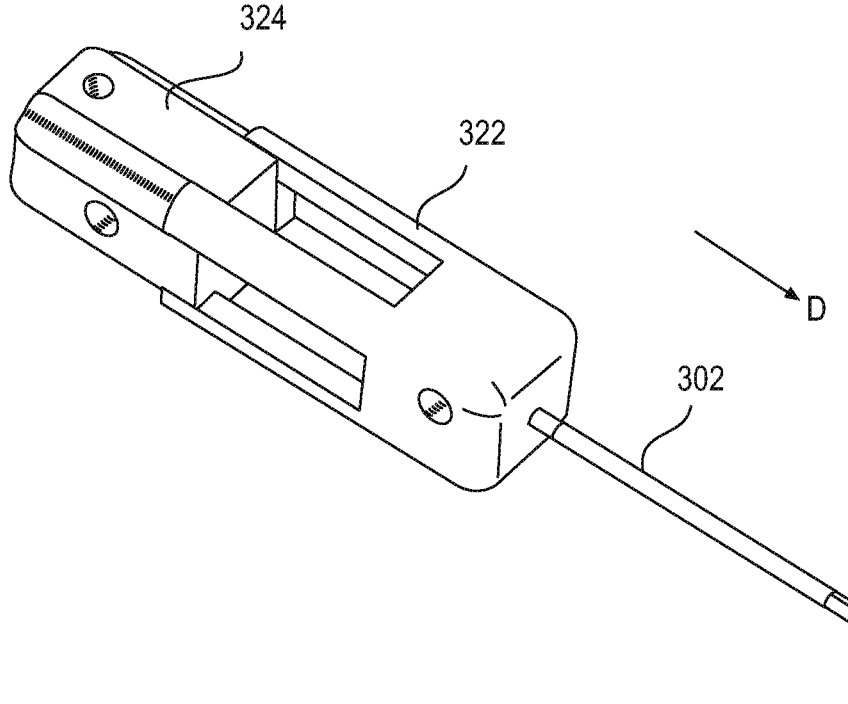
Figure 18E:
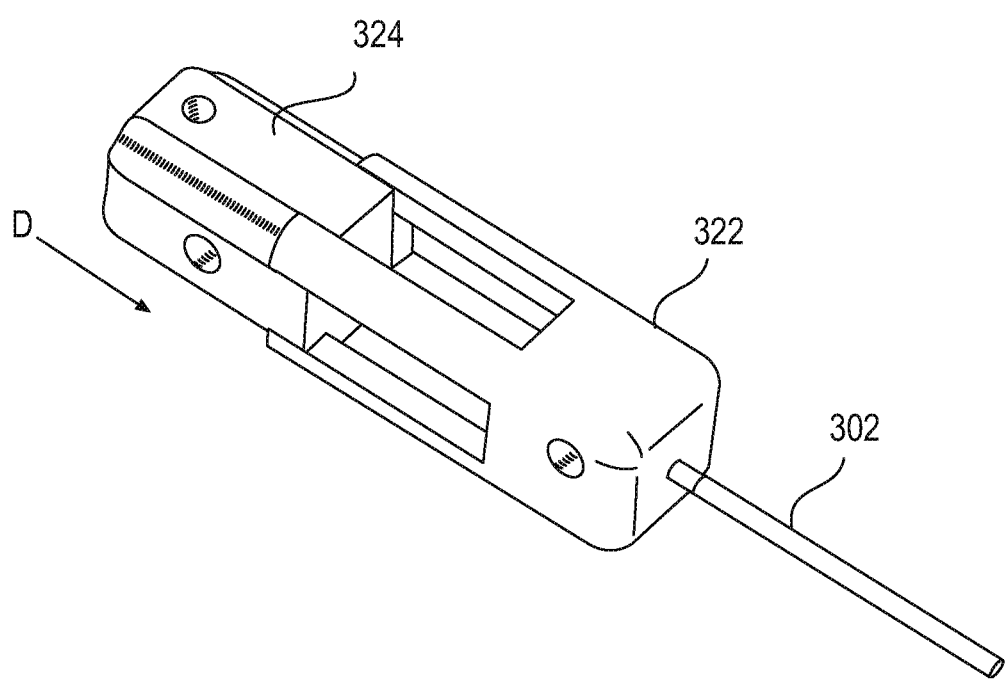

After the compressor clips are compressed to the closed (or substantially closed) position shown in FIG. 18C, outer tube actuator 322 is advanced distally in the direction of arrow D (shown in FIG. 18D) and inner sleeve actuator 324 is held in place. The movement of outer tube actuator 322 causes the outer sleeve to be advanced distally over the inner sleeve (which is held in place). The inner sleeve could also be retracted proximally while the outer tube is held in place. Advancing the outer tube displaces the compressor clips in the distal direction, which also move relative to the inner sleeve. The outer tube is advanced until the inner sleeve (and therefore the lens) is disposed within the outer tube, as shown in FIG. 18E. During this loading step sliding occurs between the outer tube and the inner sleeve, not between the lens and the inner sleeve. This minimizes shear and tensile forces acting on the lens.

The outer tube is then advanced through an incision made in the eye. To deploy the lens from the delivery system and into the lens capsule, inner sleeve actuator 324 is advanced distally in direction D. This causes inner sleeve to be advanced distally relative to the outer tube. As the inner sleeve emerges from the distal end of the outer tube, the inner sleeve will begin to split along the slit and the lens will begin to expand. The lens can therefore be delivered into the capsule.

The outer tube is generally rigid and in one embodiment is a stainless steel tube. The inner sleeve is generally a flexible material and in one embodiment is PTFE. The compressor clips can be any suitably rigid material.

Increasing the outer tube volume increases the volume into which the lens can be compressed. It is generally desirable for the outer tube to have the largest cross sectional area possible while still allowing the outer tube to be advanced into the smallest incision possible. It has been found than using an outer tube in which the cross section is generally elliptically-shaped allows the largest cross sectional area through the smallest incision.

In an alternative embodiment the inner sleeve as shown in FIGS. 18A-18E can be replaced with a rolled sheet such as inserter 64 shown in FIGS. 15-17. The system would work similarly to the described above in references to FIG. 18A-18E.

Figure 19:
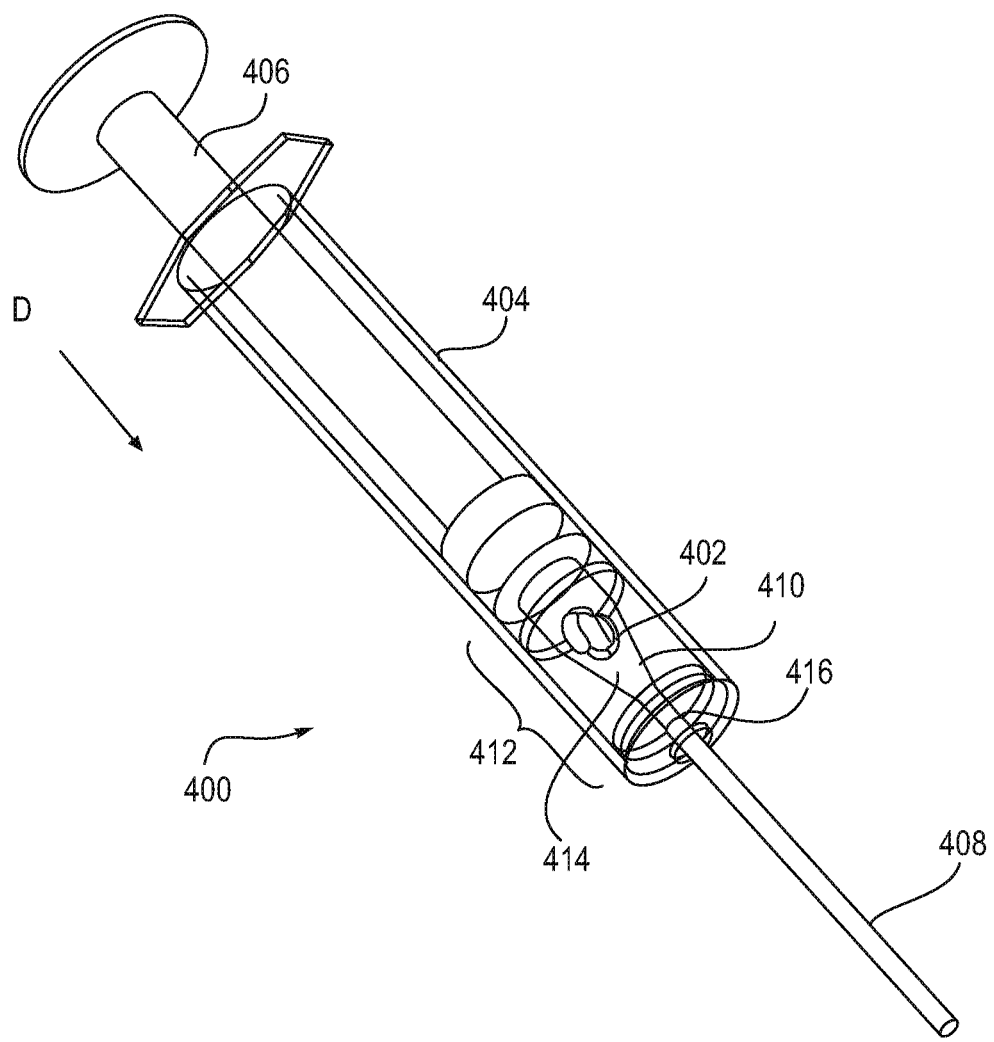
FIG. 19 shows an exemplary hydraulic loading system for loading an intraocular lens.
Figure 20:
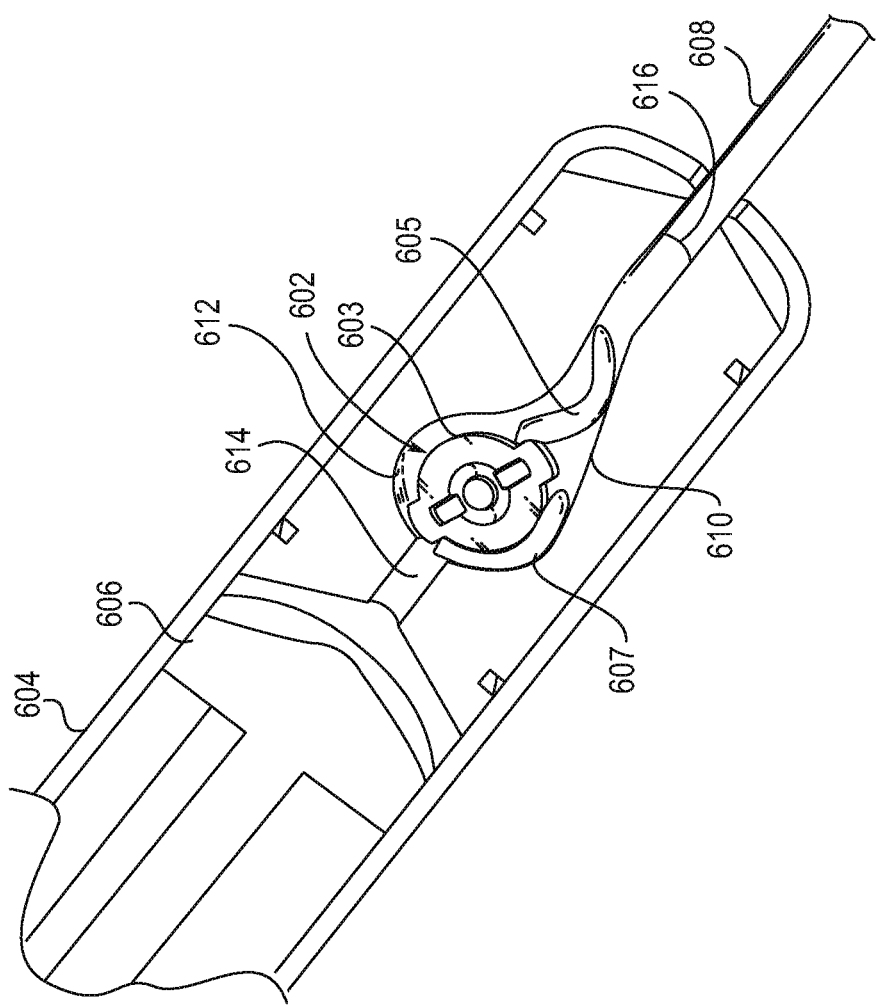
FIG. 20 illustrates an alternative hydraulic loading system for loading an intraocular lens.
Figure 21:
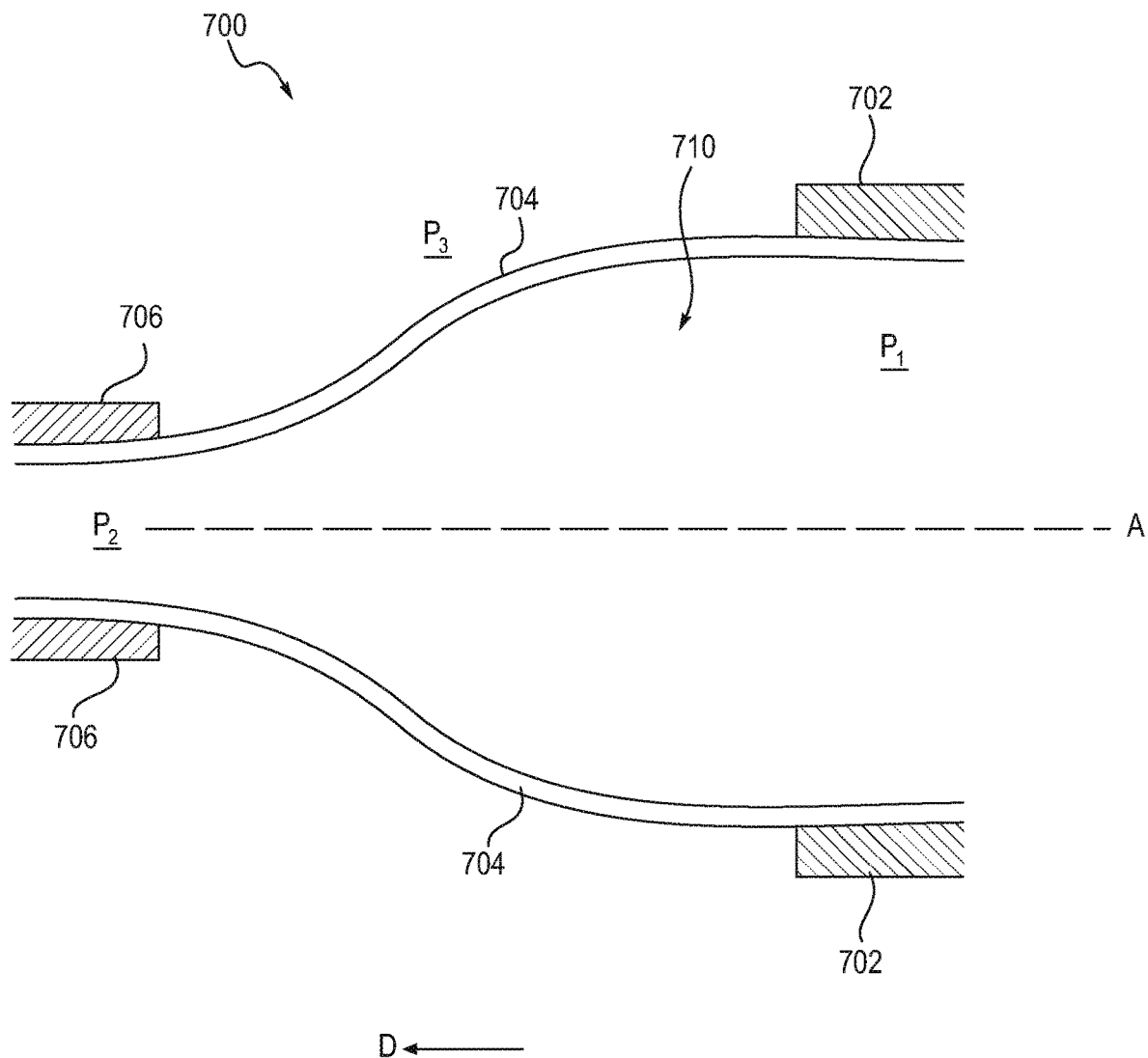
FIG. 21 illustrates an exemplary peristaltic loading concept.

FIGS. 19-21 show alternative embodiments of a hydraulic lens loading system. Using a hydraulic system to load the intraocular lens into the delivery device (as well as a hydraulic system to deploy the intraocular lens) minimizes shear and tensile forces on the lens. The lens is forced into a delivery device using a generally lubricous liquid or fluid, which minimizing shear and tensile forces acting on the lens as it is compressed and elongated. FIG. 19 shows loading system 400 for loading intraocular lens 402 into loading tube 408. The system includes syringe 404 including plunger 406. Distal region 412 of syringe 404 includes a tapered inner surface 410 which has a smaller cross sectional diameter at the distal end than at the proximal end. The distal region of the syringe contains the lens as well as fluid 414. The fluid can be a liquid such as saline and can include or can be a known viscoelastic lubricant such as, for example without limitation, aqueous solutions of sodium hyaluronate, hydroxypropylmethyl cellulose, and chondroitin sulfate.

To advance the lens into loading tube 408, the plunger is actuated in the distal D direction which causes fluid 414 and lens 402 to be advanced distally towards loading tube 108. The plunger continues to be advanced distally until the lens is forced through proximal end 416 of loading tube 108. By moving the lens with a lubricious material, shear and tensile forces on the lens are minimized.

FIG. 20 shows an alternative hydraulic loading system 600 for loading intraocular lens 602 into loading tube 608. The system is similar to previous embodiments and includes syringe 604 with plunger 606. The syringe includes lens chamber 612 which has a generally circular shape to retain the generally circular shape of lens 602. The syringe also includes tapered section 610 which directs the lens into loading tube 608. Lens 602 is initially positioned in lens chamber 612 with distal haptic 605 extending distally from optic portion 603 and into tapered section 610 while proximal haptic 607 is not extending proximally from optic portion 603. This initial positioning helps direct the lens into a compressed configuration within loading tube 608 (which includes proximal end 616) when fluid 614 is forced through lens chamber 612. The plunger is advanced distally to direct a fluid through lens chamber 612, which forces lens 602 into loading tube 608.

In an alternative design the intraocular lens can be loaded into the loading tube under vacuum pressure.

After the lens is loaded into the loading tube, the lens is hydraulically delivered into the eye. The loading tube is first detached from the loading apparatus. The loading tube is then inserted through an incision in the eye and a fluid (such as a lubricious fluid) is directed through the loading tube to eject the lens from the loading tube and into the eye. Hydraulic deployment also minimizes shear and tensile forces acting on the lens. A syringe can be used to direct the fluid through the loading tube. Alternatively, a small piston drives down the tube, pushing a short column of fluid distally to the piston. The piston is controlled with an actuator such as a knob, lever, ratchet, etc. The piston can be attached to either end of the loading tube. This means the lens can be ejected from the same end in which it is loaded, or it can be deployed from the other end of the loading tube.

FIG. 21 illustrates an alternative loading system concept using peristaltic movement to load an intraocular lens (not shown). In this design, purely compressive loads on the lens are separated in time from shear loads on the lens. The lens is "inched" along into a fully compressed state. System 700 includes rigid large tube 702, rigid small tube 706, and flexible tube 704 with a generally conical or tapered shape. Fluid 710 is contained within the system to lubricate the system and also to help push the lens through the system. The lens is moved from the rigid large tube 702 through flexible tube 704 and into a fully compressed state within small rigid tube 706. Large tube 702 has a larger diameter than small tube 706. There is generally a pressure gradient between P1 and P2 with P1 being higher. The difference in pressure between P1 and P2 (which is the driving pressure) is equal to P1 minus P2. The pressure P3 from a compressive force on the flexible tube is used to compress the lens in a direction that is substantially orthogonal to the axis A. P3 is pulsed out of phase from the driving pressure, which is also pulsed. To load the lens, P3 is initially increased to compress the lens radially. Then P3 is decreased while the driving pressure is increased, so the device is pushed in the direction D a small distance and reexpands radially. When P3 is decreased the flexible wall moves radially away from the lens and shear forces are reduced. P3 is then increased again, compressing the lens radially. P3 is then decreased as the driving pressure is increased, which again moved the lens in the direction D. The lens is therefore moved in small increments in the distal direction D, compressing it as it moves. This movement is repeated until the lens is fully compressed within small tube 706. The lens can then be deployed using any of the methods described herein.

In any or all of the embodiments described herein, the method of delivery includes creating a wound in the eye which generally comprises an incision in the eye. In some embodiments the incision is about 4 mm and preferably about 3.7 mm. The incision can, however, be slightly larger or smaller.

In any of the embodiments described herein, the position and/or orientation of the IOL may need to be adjusted for the loading step. For example, when loading an IOL with haptics, it may be necessary to align the haptics so they are oriented generally along the longitudinal axis of the delivery device before compressing the lens (see, for example, FIG. 18B). Alternatively, only one haptic may be straightened while a second haptic can be positioned peripherally around the optic portion (see, for example, FIG. 20). These orientations can provide for a better delivery profile and minimizes the chance of damage to the IOL during deployment.

To compress any of the fluid-filled accommodating IOL described herein, it may be necessary to apply a compressive side force of about 0.5 pounds. This can vary, however, depending on the size, composition, and volume of the IOL.

While only these embodiments have been described, they all attempt to minimize the amount of shear and tensile forces acting on the IOL during the loading and/or delivery process. One common method is minimizing the amount of sliding that occurs between the IOL and the delivery system components. Other embodiments are included in this invention which allow the IOL to be loaded into and deployed from the delivery device with (or in conjunction with) a delivery device component, in order to reduce these unwanted forces.

What is claimed is:

1. A system for deploying an intraocular lens, comprising: an intraocular lens; a delivery device comprising a fluid therein and a lens receiving area, wherein the lens receiving area holds the intraocular lens in a deformed configuration; a plunger disposed at a proximal end of the delivery device; a tapered portion at a distal end of the delivery device; and a loading tube coupled to the tapered portion, wherein the plunger is designed to be actuated in a distal direction such that actuation of the plunger causes the fluid to flow in a distal direction to force the intraocular lens into the loading tube through the tapered portion.

2. The system of claim 1, wherein the loading tube is detachable.

3. The system of claim 1, wherein the loading tube is designed to compress the intraocular lens.

4. The system of claim 1, wherein the lens receiving area is part of a lens chamber and the lens chamber is in fluid communication with a fluid delivery lumen of the delivery device.

5. The system of claim 4, wherein the lens chamber is shaped to allow a leading haptic of the intraocular lens to extend distally away from an optic portion of the intraocular lens while a trailing haptic is not extending proximally from the optic portion.

\* \* \* \* \*